(12) United States Patent
Chen

(10) Patent No.: US 11,172,964 B1
(45) Date of Patent: Nov. 16, 2021

(54) TRANSLAMINAR PEDICLE ANCHOR SUSPENSION SYSTEM AND ITS ANCHOR AND RELATED COMPONENT-SET

(71) Applicant: Chien-Yu Chen, Taipei (TW)

(72) Inventor: Chien-Yu Chen, Taipei (TW)

( * ) Notice: Subject to any disclaimer, the term of this patent is extended or adjusted under 35 U.S.C. 154(b) by 0 days.

(21) Appl. No.: 17/193,320

(22) Filed: Mar. 5, 2021

(30) Foreign Application Priority Data

Sep. 11, 2020 (TW) .................................. 109131386

(51) Int. Cl.
*A61B 17/70* (2006.01)

(52) U.S. Cl.
CPC ...... *A61B 17/7071* (2013.01); *A61B 17/7032* (2013.01); *A61B 17/7044* (2013.01); *A61B 17/7082* (2013.01)

(58) Field of Classification Search
CPC . A61B 17/70; A61B 17/7022; A61B 17/7026; A61B 17/7031; A61B 17/7062–7071; A61B 17/84; A61B 17/842
See application file for complete search history.

(56) References Cited

U.S. PATENT DOCUMENTS

| | | | |
|---|---|---|---|
| 6,358,254 B1* | 3/2002 | Anderson .......... | A61B 17/1671 606/103 |
| 2007/0088358 A1* | 4/2007 | Yuan .................. | A61F 2/4405 606/279 |
| 2007/0299445 A1* | 12/2007 | Shadduck .......... | A61B 17/7067 606/86 A |
| 2010/0185239 A1* | 7/2010 | Patel ................. | A61B 17/7071 606/246 |
| 2010/0241164 A1* | 9/2010 | Fischer ............. | A61B 17/7064 606/247 |
| 2011/0313465 A1* | 12/2011 | Warren ............. | A61B 17/8685 606/279 |
| 2017/0007299 A1* | 1/2017 | Mundis, Jr. ....... | A61B 17/7082 |
| 2017/0079693 A1* | 3/2017 | Cheng .............. | A61B 17/7067 |
| 2018/0098799 A1* | 4/2018 | Songer ............. | A61B 17/7083 |
| 2020/0000505 A1* | 1/2020 | Vitale .............. | A61B 17/7052 |

* cited by examiner

*Primary Examiner* — Eduardo C Robert
*Assistant Examiner* — Michelle C Eckman

(57) ABSTRACT

A translaminar pedicle anchor suspension system (referred as T-PAS system) applicable to vertebral surgeries is disclosed. The T-PAS system comprises: at least one pedicle anchor capable of being fixed to a pedicle of a lower vertebral segment, at least one suspension ligament having one end thereof fixed to the pedicle anchor, and at least one washer capable of fixing the other end of the suspension ligament to a contralateral side of a lamina of an upper vertebral segment. By using the suspension ligament to suspend the upper vertebral segment via a tunnel drilled on the lamina, not only the spine can be dynamically stabilized, but also the use of traditional pedicle screws and bone fusion can be avoided.

15 Claims, 25 Drawing Sheets

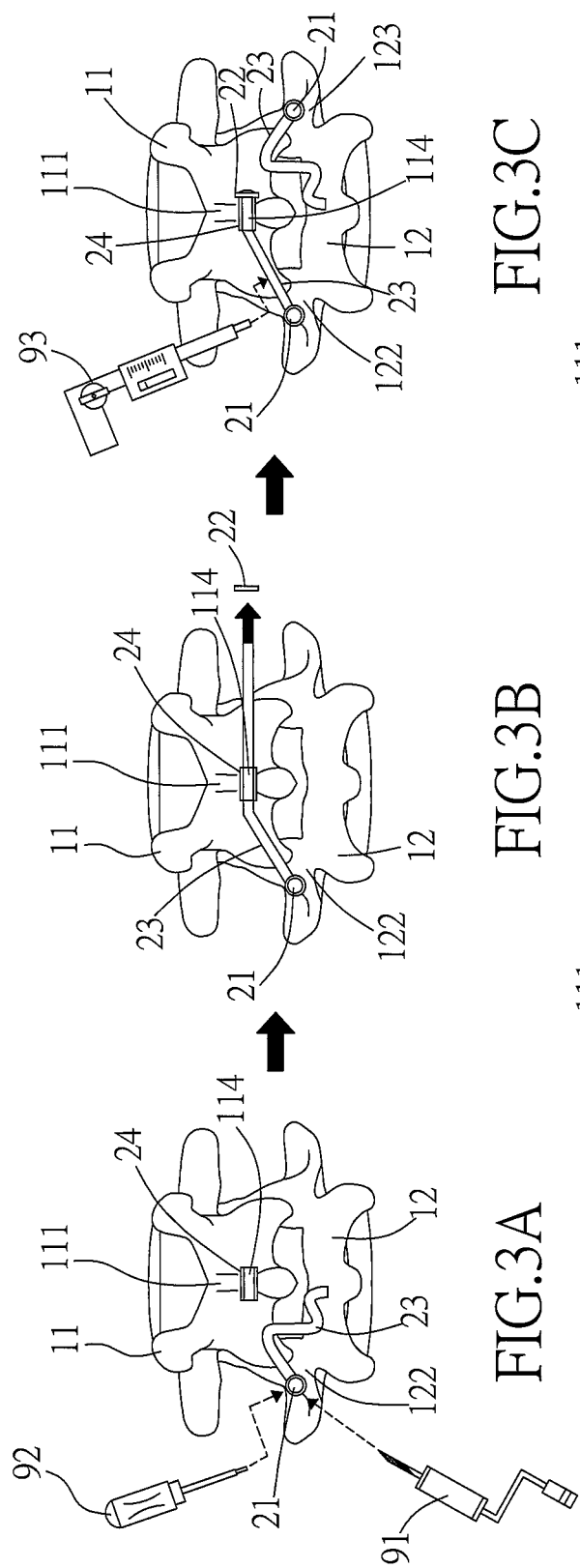

A-A section

TRANSLAMINAR PEDICLE ANCHOR SUSPENSION SYSTEM AND ITS ANCHOR AND RELATED COMPONENT-SET

BACKGROUND OF INVENTION

1. Field of the Invention

The invention refers to a translaminar pedicle anchor suspension system (referred as T-PAS system hereinafter), especially refers to a system, a pedicle anchor and related component-set thereof that can be used to suspend a vertebral segment above from an adjacent segment below by means of a "pedicle anchor and artificial ligament" construct.

2. Description of the Prior Art

The human spine is composed of twenty-four vertebrae (including seven cervical vertebrae, twelve thoracic vertebrae and five lumbar vertebrae), one sacrum and one coccyx connected by ligaments, joints and intervertebral discs. When one of the vertebrae is displaced, slipped, deformed, degenerated or damaged due to diseases or trauma, it may cause pain or neurological symptoms as a result of advanced degeneration, instability or nerve compression.

Surgery is usually indicated whenever conservative treatment fails to relieve the symptoms of pain or neurologic deficit. Common surgical procedures may include: decompressive laminectomy, discectomy, fusion with or without instrumentation.

Current practice in spine surgery often requires the use of rigid spinal instrumentation to achieve immediate stability and to facilitate fusion. A typical conventional spinal fixator well-known in the art comprises the use of at least four pedicle screws and two connecting rods to stabilize the two adjacent vertebral segments, but the disadvantages of spinal instrumentation may include: 1. Nerve injury; 2. Increased bleeding; 3. Prolonged operative time; 4. Pedicle screw loosening; 5. Subsequent development of adjacent segment stenosis; 6. Loss of natural flexibility of spine; 7. Chronic back pain; 8. Bulky and protruding implant screw heads or rods may cause pain due to soft tissue impingement and bursitis.

Therefore, the present invention discloses the T-PAS system, which aims to reconstruct facet capsular ligaments with the use of a "pedicle anchor and suspension ligament" construct to dynamically stabilize the facet joints and to minimize the unwanted complications from the conventional instrumented fusion procedures.

SUMMARY OF THE INVENTION

The primary objective of the invention is to provide a "Translaminar Pedicle Anchor Suspension" system (referred to as T-PAS system), in which a loop of artificial ligament (also referred to as suspension ligament) was pulled to the contralateral side of lamina through a transverse tunnel created through a rigid point of the arch of lamina, and a pig-nose washer was used to cinch the suspension ligament on the contralateral wall of lamina of the upper segment. The loop of suspension ligament was pulled to stabilize the pig-nose washer on the contralateral wall of the lamina, and the suspension ligament was subsequently tightened by a pedicle anchor, which located at the adjacent segment below, to achieve optimal tension of the ligament.

The procedure is easy and the suspension pedicle anchors are smaller and shorter compared with conventional instrumentation using "Pedicle screw and Rod" systems. The low profile of the system and the ease of its application can obviously prevent complications of conventional pedicle screws which include excessive bleeding, nerve injury, screw loosening, and accelerated degeneration of adjacent segments.

Another objective of the invention is to provide the pedicle anchor of the T-PAS system, which is formed with a novel oblique through-hole. The pedicle anchor not only can fix one end of the suspension ligament to the pedicle of the lower vertebral segment, but also, through the novel design of the oblique through hole, the pedicle anchor can be rotated and screwed into the pedicle in order to pull and adjust the tension of the suspension ligament. Moreover, after the vertebral surgery is completed, the top end of the pedicle anchor will only slightly protrude or even be flush with the surface of the pedicle, which can minimize the patient's foreign body sensation and discomfort.

The transverse laminar tunnel is created with a 2 mm burr head through a point which is usually located between the upper ¼ to ⅓ of the roof of the lamina. The tunnel allows passage of suspension ligaments from both sides to be tightened by suspension pedicle anchors from a segment below. An optimal tension can be achieved as the pedicle anchor is placed further down, the optimal tension can be measured by a tension gauge or felt by the finger of a surgeon. The optimal tension is defined by observing the movement of facet joints of less than 1 mm when the base of lamina of the upper segment was pulled and tested with a towel clip.

A further objective of the invention is to provide a component-set of the T-PAS system, which allows the surgeon to perform the procedure with ease, and to reduce the operative time which is beneficial especially to the elderly patients.

In order to achieve the aforementioned objectives, the invention provides a translaminar pedicle anchor suspension system (referred as T-PAS system) capable of being configured to be installed on a spine having at least an upper vertebral segment and a lower vertebral segment; the T-PAS system comprises: at least one pedicle anchor, capable of being configured to be fixed to one of two pedicles of the lower vertebral segment; and at least one suspension ligament, one end of the suspension ligament being fixed to the pedicle anchor and thus configured to be fixed to the pedicle of the lower vertebral segment, the other end of the suspension ligament being connected to a contralateral side (surface) of a lamina of the upper vertebral segment by a connecting means (such as a washer); in addition, the suspension ligament being tightened to a predetermined tension, and the suspension ligament being capable of dynamically stabilizing and suspending the upper vertebral segment to the segment below with the "pedicle anchor and suspension ligament" construct.

In a preferred embodiment, each of the upper vertebral segment and the lower vertebral segment respectively includes: said lamina and two said pedicles respectively located on left and right sides of the lamina; the lamina of the upper vertebral segment is prepared providing a tunnel penetrating left and right side-surfaces of the lamina. The T-PAS system further comprises a washer which is configured to be located at the tunnel opening on the side of the lamina of the upper vertebral segment; the washer has a size greater than the diameter of the tunnel. The connecting means is to pass the free end of the suspension ligament through the tunnel of the lamina of the upper vertebral segment and then secure the suspension ligament looping it around the washer. Since the size of the washer is greater than the diameter of the tunnel, the suspension ligament can be tensioned pulling the washer against the lamina wall at the opening of the tunnel in the upper vertebral segment.

In a preferred embodiment, at least two pedicle anchors are used, which are configured to be respectively installed into the two pedicles of the lower vertebral segment; said two pedicles includes a left pedicle and a right pedicle; at least two washers are used, which are configured to be respectively located at left and right ends of the tunnel of the lamina of the upper vertebral segment; at least two suspension ligaments are used; in which one end of the first suspension ligament is fixed to the pedicle anchor located in the left pedicle, while the other end of the same suspension ligament is configured to first pass through the tunnel from the left side-surface of the lamina to the right side-surface of the lamina of the upper vertebral segment, and then the suspension ligament is connected to the washer located on the right side-surface of the lamina; on the other side, one end of the second suspension ligament is fixed to the pedicle anchor located in the right pedicle, while the other end of the second suspension ligament is configured to first pass through the tunnel from the right side-surface to the left side-surface of the lamina of the upper vertebral segment, and then the suspension ligament is connected to the washer located on the left side-surface of the lamina. (the Washer is on the contralateral side of laminar wall)

In a preferred embodiment, the T-PAS system further includes a hollow sleeve plugged in the tunnel.

In a preferred embodiment, the suspension ligament is an artificial ligament; the pedicle anchor is a screw with external thread; the size of the washer is larger than the diameter of the tunnel.(laminar tunnel)

In a preferred embodiment, the pedicle anchor has an elongated columnar body extending along a central axis, an external thread arranged on the outer surface of the columnar body, a fitting structure arranged at a top end of the columnar body, and an oblique through hole penetrating through the columnar body; wherein, the oblique through hole passes through the central axis; openings at two ends of the through hole are respectively called the upper opening and the lower opening; a distance between the upper opening and the top end of the columnar body is smaller than another distance between the lower opening and the top end of the columnar body; the oblique through hole (off-set eyelets) allows the suspension ligament to pass through, so that the pedicle anchor can be hung on the suspension ligament; the fitting structure can be connected with a screwdriver, such that, by operating the screwdriver, the pedicle anchor is driven to rotate about the central axis, and the pedicle anchor can be screwed and fixed to the pedicle In a preferred embodiment, the external thread provided on the outer surface of the columnar body of the pedicle anchor includes a smaller-pitched threaded portion and a larger-pitched threaded portion; the smaller-pitched threaded portion is located closer to the top end of the columnar body; the larger-pitched threaded portion is located away from the top end of the columnar body.

In a preferred embodiment, the suspension ligament is folded into a double-line side-by-side structure and has said closed end at the folded section and said open end away from the folded section; a way to pass the suspension ligament through the oblique(obliquely) through hole is to pass the closed end of the folded suspension ligament into the oblique through hole through the upper opening; and then the closed end of the folded suspension ligament is pulled out from the lower opening of the oblique through hole; in the meantime, the open end of the folded suspension ligament remains exposed to the outside of the upper opening.

In a preferred embodiment, a method for assembling the suspension ligament to the washer is to first pull a middle section of the suspension ligament (a loop) through the tunnel of the lamina of the upper vertebral segment; and then, form a closed end at the middle section of the suspension ligament; and then, place the closed end of the suspension ligament on a bar portion of the washer; wherein, both ends of the suspension ligament away from the closed end at the middle section are called as open ends; after that, a pulling force is applied from the open ends of the suspension ligament in order to force the washer to press against the outer side-surface near the tunnel of the lamina of the upper vertebral segment, so as to achieve the effect of combining and fixing the closed end of the suspension ligament to the lamina of the upper vertebral segment by means of the washer.

In a preferred embodiment, a method of fixing the pedicle anchor to the pedicle of the lower vertebral segment is to first pull the closed end of the folded suspension ligament out of the lower opening of the oblique through hole of the pedicle anchor; then, screw a lower part of the columnar body of the pedicle anchor into the pedicle of the lower vertebral segment in order to make the lower opening of the pedicle anchor close to but still exposed on the outer surface of the pedicle of the lower vertebral segment; then, gently apply a slight pulling force from the open end of the suspension ligament so that the suspension ligament temporarily has a relatively small first tension; and then, the pedicle anchor is again gradually screwed into the pedicle of the lower vertebral segment, such that the lower opening of the pedicle anchor is gradually embedded in the pedicle of the lower vertebral segment, and in the meantime, the suspension ligament is gradually wound around the outer surface of the smaller-pitched thread portion of the pedicle anchor and thus clamped between the outer surface of the pedicle anchor and the inside of the pedicle of the lower vertebral segment; wherein, in addition to connecting and fixing one end of the suspension ligament to the pedicle of the lower vertebral segment, the suspension ligament can be further pulled by a larger force in order to tighten up the suspension ligament to reach and maintain a relatively larger second tension; the second tension is much greater than the first tension and is the predetermined tension when the T-PAS system is completely installed.

In order to achieve the aforementioned objectives, the invention also provides a component set for use in the T-PAS system. The component set comprises: at least one pedicle anchor, at least one washer, at least one suspension ligament, and a screwdriver. The pedicle anchor can be fixed to one of two pedicles of the lower vertebral segment. The washer can be located on a lamina of the upper vertebral segment. The suspension ligament is for connecting the pedicle anchor and the washer. The suspension ligament can be fixed to both the pedicle of the lower vertebral segment and the lamina of the upper vertebral segment by means of the pedicle anchor and the washer. In addition, the suspension ligament is pre-assembled on the pedicle anchor. The screwdriver can be connected to the pedicle anchor, such that the pedicle anchor can be screwed into the pedicle of the lower vertebral segment by operating the screwdriver.

BRIEF DESCRIPTION OF THE DRAWINGS

The present invention will now be specified with reference to its preferred embodiment illustrated in the drawings, in which:

FIGS. 3A to 3E are schematic diagrams respectively showing the steps for installing the T-PAS system of the present invention onto two adjacent vertebral segments.

DESCRIPTION OF THE PREFERRED EMBODIMENT

Figure 1A:
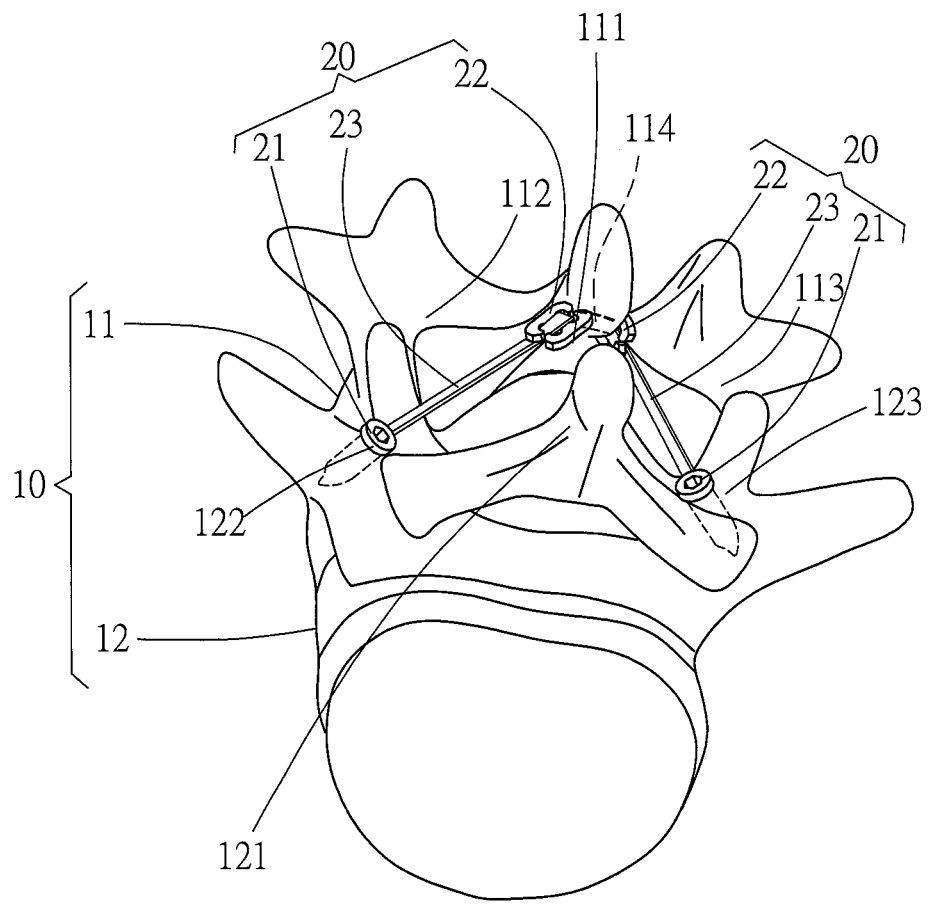
FIG. 1A and FIG. 1B respectively are the first perspective three-dimensional (3D) schematic diagram and the second perspective 3D schematic diagram of an embodiment of the T-PAS system of the present invention furnished on two adjacent vertebral segments.
Figure 1B:
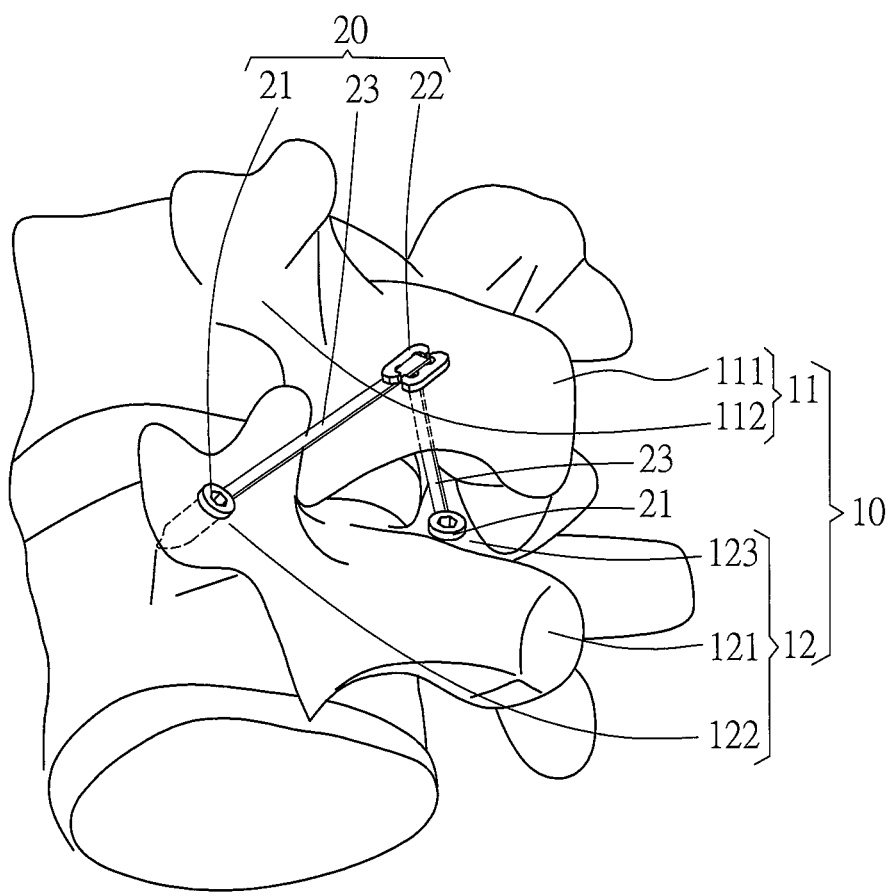
Figure 2B:
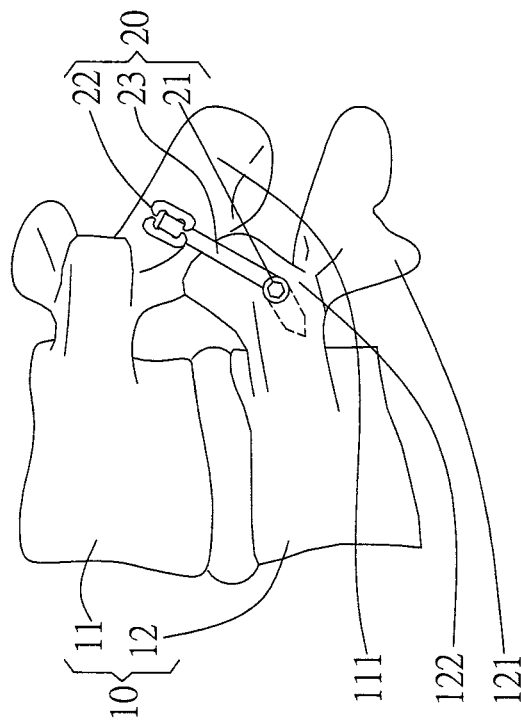
FIG. 2A and FIG. 2B respectively are the top-view schematic diagram and the left-side-view schematic diagram of an embodiment of the T-PAS system of the present invention furnished on two adjacent vertebral segments.
Figure 2A:
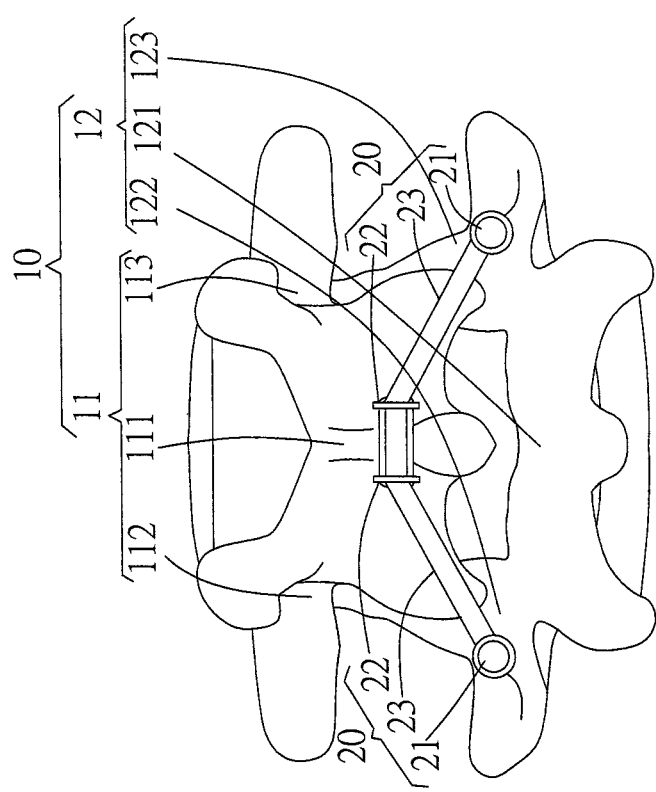

The present invention refers to a translaminar pedicle anchor suspension system (referred as T-PAS system) applicable to vertebral surgeries. The T-PAS system comprises: at least one pedicle anchor capable of being fixed to a pedicle of a lower vertebral segment, at least one suspension ligament having one end thereof fixed to the pedicle anchor, and at least one washer capable of fixing the other end of the suspension ligament to a contralateral side of a lamina of an upper vertebral segment. The suspension ligament is tightened to a predetermined tension, and the upper vertebral segments are suspended by the suspension ligament to a segment below. By using the suspension ligament to suspend the upper vertebral segment via a tunnel drilled on the lamina, not only can the spine be dynamically stabilized, but also the use of traditional pedicle screws and bone fusion can be avoided. This novel T-PAS system has the following advantages: (1) reduce operation time; (2) reduce the risk of nerve damage; (3) reduce bleeding; (4) maintain vertebral mobility; (5) patients would feel more natural without stiffness in the lower back after surgery; and (6) it can theoretically avoid the accelerated degeneration of adjacent segments caused by internal fixation and fusion, which is not an uncommon complication after conventional instrumented fusion. The indications and scopes of application of the T-PAS system of the present invention include (but are not limited to): single or multiple joint stenosis, lumbar spine stenosis, lumbar spondylolisthesis, and etc. The T-PAS system of the present invention can be applied to the patient's first primary surgery after decompressive surgery, or it can be used in the subsequent treatment of junctional stenosis without having to remove the instrumentation.

In the T-PAS system of the present invention, a loop of artificial ligament (suspension ligament) was pulled to the contralateral side of lamina through a transverse tunnel created through a rigid point of the arch of lamina, and a pig-nose washer was used to cinch the suspension ligament on the contralateral wall of lamina of the upper segment. The loop of suspension ligament was pulled to stabilize the pig-nose washer on the contralateral wall of the lamina, and the suspension ligament was subsequently tightened by a pedicle anchor, which located at the adjacent segment below, to achieve optimal tension of the ligament. Such procedure is easy and also the suspension pedicle anchors are smaller and shorter compared with conventional instrumentation using "Pedicle screw and Rod" systems. The low profile of the system and the ease of its application can obviously prevent complications of conventional pedicle screws which include excessive bleeding, nerve injury, screw loosening, and accelerated degeneration of adjacent segments.

The following descriptions provide some fundamental illustrations for the Key words, Instruments, Indications, Benefits, and Surgical Techniques regarding to the T-PAS system of the present invention.

Key Words:
1. (T-PAS) Translaminar Pedicle Anchor Suspension: A surgical procedure where dynamic stabilization is provided for two adjacent lumbar segments, and it is performed with anchors in the pedicles and a suspension ligament passed through a laminar tunnel.
2. Suspension Pedicle Anchor (SPA): Threaded Screws with offset or level eyelets containing Suspension ligaments (SL). Sizes: (4.5×25 mm) (5×30 mm)
3. Suspension Ligament (SL): 2-3 mm diameter material threaded through the eyelets of the Pedicle Anchor.
4. Laminar Pig-Nose Washer (LPNW) with Slots on both sides: (Single-central column, Double-central column)
5. Laminar Banana Washer: (Unilateral procedures and Endoscopic procedure of spine)
6. Suspension Abutment Pedicle Anchor (SAPA): A Pedicle Anchor that is placed adjacent to an existing Pedicle Screw. That is, the SAPA is shaped like a SPA with shorter length and smaller diameter for ASD in which the instrumentation from primary surgery is left unremoved.
7. Headed Suspension Pedicle Anchor (HSPA): A fixed or polyaxial headed Pedicle Anchor with eyelets to pass a (SL) through and attachment on the top for a fusion rod.
    Instruments:
1. Pedicle Anchor Driver: Used to insert the anchor with offset Suspension Ligament hangers.
2. Suspension Ligament Off-Set Passer: To pull the SL through the Laminar Tunnel.
(Optional: Curved needle or Wire Passer to pull the SL through the Laminar Tunnel)
3. Off-Set Burr Hole Tap: To enlarge and smooth the drill hole.
4. Laminar Drill Guide: To create the Laminar Tunnel for the Suspension Ligament.
    (Optional: Use an angled burr or straight burr with 2 mm burr head)
5. Ligament tension gauge: To assess the tension of the SL.
    1. Indications:
A. Primary indications
B. Extended indications
    A. Primary Indications:
1. Degenerative Lumbar Spine Stenosis: Single or multi-level, with or without disc herniation.
2. Degenerative Spondylolisthesis: Single or multiple motion segments.
3. Discectomy that Destabilizes a Facet Joint: Instability created during discectomy and decompression.
4. Discectomy with a Preexisting Instability: Known instability at the level of a disc herniation.
(i.e. Spondylolisthesis or instability detected on flexion & extension films)
    B. Extended Indications
1. Prevention of Junctional Stenosis: Using a "Headed Suspension Pedicle Anchor" (HSPA) as the upper screws of an instrumented fusion construct in primary surgery, to create a dynamically stabilize junctional segment above.
2. Treatment of Junctional Stenosis Above an Instrumented Fusion: Using a "Suspension Abutment Pedicle Anchor" (SAPA) technique to preserve the instrumented fusion construct in revision surgery while dynamically stabilizing the segment above the fusion.
    2. Benefits of Intersegmental Suspension Technique:
1. Preserves motion of the lumbar spine, theoretically reducing or preventing the accelerated junctional degeneration of adjacent segments, which is not uncommon in instrumented fusion technique.
2. Prevents the unwanted discomfort from instrumented fusion, including chronic back pain, stiffness, loosening of screws, and nerve injury.
3. Reduces incidence of nerve injury or blood transfusion because of the small sized Pedicle Anchor, and the ease of application with the T-PAS technique.
4. Less epidural manipulation and less bleeding from epidural vessels, in contrast to interbody cage placement with an instrumented fusion.
    3. Surgical Techniques: A, B and Extended Indication Technique
        Technique A: "Off-Set Eyelet" Pedicle Anchor
1. With the patient prone on a spine frame under general anesthesia, an incision is made to expose the L4 and L5 laminae and bilateral L4/5 facets with care to protect the midline ligamentous structures.
2. A planned and limited laminotomy is performed. This includes excision of part of the thickened laminae of the lower part of L4 and the upper part of L5, the hypertrophic ligamentum flavum, and the medial portion of the L4/5 facet (medial edge of superior facet) to decompress the L5 nerve roots bilaterally. The midline ligamentous structures are carefully preserved, including the supraspinous and interspinous ligaments.
The outer border of L4/5 facets were defined by cautery, and the orientation of the superior facet and pedicle are identified. The midline ligamentous structures are carefully preserved, including the supraspinous and interspinous ligaments.
3. A Pedicle Anchor (PA), which is 30 mm long with a diameter of 4.5 mm and pre-threaded with a 2 mm Suspension Ligament (SL), is placed into the L5 pedicle in usual manner. This anchor will be buried to the first eyelet level in the anchor (which is 10 mm below the screw top) to achieve the "FIRST INTERFACE FIXATION" of the Suspension Ligament.
4. A 2 mm diameter "Laminar Tunnel" is created through the K-point ("Kenyoh Point") with a 2 mm burr head and the tunnel is then smoothed and slightly widened with Burr hole tap to facilitate passage of the Suspension Ligament across the tunnel.
"K-Point": Located at the intersection of the spinous process in the sagittal plane, and the lamina in the coronal plane. The K-point is located at the rigid part of the base of lamina which is usually the junction of superior ¼ and middle ⅓ of the arch of the lamina.
5. A 2 mm diameter burr head is used to create the laminar tunnel hole at the "K-Point" to pass the Suspension Ligament through the bone tunnel. The tunnel is smoothed and slightly enlarged with an "Off-Set Laminar Drill-Hole Tap". (Steps 4 and 5 repeated) . . .
6. The Suspension Ligament Passer (or use a round bodied suture needle) is now used to pull the Suspension Ligament as a loop, through the "Laminar Tunnel" to the contralateral side. The free end of Suspension Ligament remains on the Suspension Pedicle Anchor side.
7. A "Laminar Pig-Nose Washer" (LPNW) is used to secure the loop of the Suspension Ligament on the contralateral side of the lamina. The loop of the Suspension Ligament is placed into both slots of LPNW and then the free end of the Suspension Ligament is pulled tight cinching the LPNW against the opposite side lamina.
8. The returning free end of the Suspension ligament (SL) is brought under and below the first strand. Particularly, an extra length of the SL was pulled up according to the estimated length of the SL and the diameter of the screw before tightening down the SPA before the upper eyelet was buried below the bone surface. The SL is then pulled and tensioned while the pedicle anchor is then tightened down, so the second eyelet, which is 5 mm above the lower eyelet and is 5 mm below the top of anchor, is buried below the bone surface to achieve a "SECOND INTERFACE FIXATION" of the SL. This locks both ends of the SL between the anchor and the bone.

9. The tension of the SL can now be measured with a tension gauge or evaluated with the surgeon's finger by palpation. If more tension is required, the PA can further be tightened downward after both ends of SL are cut.

10. The same procedure is repeated on the contralateral side when bilateral suspension is indicated.

11. The translaminar pedicle ligament suspension procedure of is then completed, and the wound is closed in the usual manner with or without drains.

Postoperative Care

Patients are advised to use a soft lumbar corset is for 4-6 weeks, and motion of lumbar spine is not restricted.

Technique B: "Level Eyelet" Pedicle Anchor

1. With the patient prone on a spine frame under general anesthesia, an incision is made to expose the L4 and L5 laminae and bilateral L4/5 facets with care to protect the midline ligamentous structures.

2. A planned and limited laminotomy is performed. This includes excision of part of the thickened laminae of the lower part of L4 and the upper part of L5, the hypertrophic ligamentum flavum, and the medial portion of the L4/5 facet (medial edge of superior facet) to decompress the L5 nerve roots bilaterally.

The outer border of L4/5 facets were defined by cautery, and the orientation of the superior facet and pedicle are identified. The midline ligamentous structures are carefully preserved, including the supraspinous and interspinous ligaments.

3. A Suspension Pedicle Anchor (SPA), which is 30 mm long with a diameter of 5 mm and pre-threaded with a 2 mm Suspension Ligament (SL), is placed into the L5 pedicle in usual manner. The level eyelets which are 5 mm below the top of the screw are left exposed above the bony surface of the pedicle.

4. A 2 mm diameter "Laminar Tunnel" is created through the K-point ("Kenyoh Point") with a 2 mm burr head to create a hole to pass the Suspension Ligament across.

"K-Point": Located at the arch of laminate which is "at the intersection of the spinous process in the sagittal plane, and the lamina in the coronal plane". It is usually located at the junction of superior ⅓ and middle ⅓ of the arch of the lamina in the thin section of the bone.

5. The Laminar Tunnel is smoothed and slightly enlarged with an "Off-Set Laminar Drill-Hole Tap". A 2 mm diameter burr head is used to create the laminar tunnel hole at the "K-Point" to pass the Suspension Ligament through the bone tunnel.

6. The Suspension Ligament Passer (or a round bodied suture needle) is now used to pull a loop of the Suspension Ligament through the "Laminar Tunnel" to the contralateral side. The free ends of Suspension Ligament remain on the Pedicle Anchor side.

7. A "Laminar Pig-Nose Washer" (LPNW) is used to secure the loop of the Suspension Ligament on the contralateral side of the lamina. The two strands of the loop of the Suspension Ligament are placed around each slot of LPNW. And then, the free end of the Suspension Ligament on the pedicle anchor side is brought under and below the first strand. Both strands of the SL are then pulled tightly tensioning the construct 8. With the tension maintained on both free ends of SL, the returning end is passed under the Suspension Ligament on the ipsilateral side of the anchor. The appropriate tension is applied as the pedicle anchor is then tightened down with both eyelets secured under bone creating an interface fixation. The Suspension Ligament is secured on the contralateral side of the lamina by the LPNW.

9. The Pedicle Anchor can be driven further down when additional tension is required.

10. The same procedure is repeated on the contralateral side to achieve bilateral Pedicle Anchor suspension.

11. The translaminar pedicle ligament suspension procedure is then completed, and the wound is closed in the usual manner with or without drains.

Postoperative Care

Patients are advised to use a soft lumbar corset is for 4-6 weeks, and motion of lumbar spine is not restricted.

B. Extended Indication Techniques

Dynamic Stabilization of Adjacent Segments of a Rigid Lumbar Fusion

Providing Prevention and Treatment of "Adjacent Segment Degeneration" (ASD)

1. PREVENTION OF A.S.D.: Use a Headed Suspension Pedicle Anchor (HSPA). This screw will accommodate the rod for the fusion to the lower segment and provide an eyelet with the Suspension Ligament to dynamically stabilize the segment above the fusion, using technique of A or B.

2. TREATMENT OF A.S.D.: Use a Suspension Abutment Pedicle Anchor (SAPA) placed in the same Pedicle where the upper pedicle screw is located in an instrumented fusion construct that has progressive disease in the level above the fusion. The SAPA is placed adjacent to the current pedicle screw through the technique of Cortical Bone Trajectory or from Superiorly as long as the SAPA can be securely anchored. Once an SAPA is placed securely in the pedicle with instrumented fusion, the T-PAS Procedure can then be repeated for the Adjacent Segment as described using technique A or B.

In order to more clearly illustrate the T-PAS system and its pedicle anchors and component-set proposed by the present invention, the following embodiments will be described in detail with the drawings.

Please refer to FIG. 1A, FIG. 1B, FIG. 2A and FIG. 2B, which respectively are the first perspective three-dimensional (3D) schematic diagram, the second perspective 3D schematic diagram, the top-view schematic diagram, and the left-side-view schematic diagram of an embodiment of the T-PAS system of the present invention furnished on two adjacent vertebral segments.

The translaminar pedicle anchor suspension system (referred as T-PAS system) of the present invention can be installed on a spine 10 having at least an upper vertebral segment 11 and a lower vertebral segment 12. Each of the upper vertebral segment 11 and the lower vertebral segment 12 respectively includes: a lamina 111, 121 and two pedicles 112, 113, 122, 123 which are respectively located on the left and right sides of the lamina 111, 121. In this embodiment, the T-PAS system 20 is installed on the L4 and L5 vertebrae of the lumbar spine of the spine 10 as an example for description, however, it can also be installed on vertebrae at different positions, or used to connect and suspend a larger number of vertebrae (such as three or more layers of vertebrae).

As shown in FIG. 1A, FIG. 1B, FIG. 2A and FIG. 2B, the T-PAS system 20 of the invention comprises: at least one pedicle anchor 21, at least one washer 22 and at least one suspension ligament 23. The pedicle anchor 21 is capable of being fixed to one of the pedicles 122 of the lower vertebral segment 12. The washer 22 is located near a side-surface of the lamina 111 of the upper vertebral segment 11; particularly, the washer 22 is preferably located at a location of the lamina 111 with the greatest strength or thickness. In an embodiment of the present invention, one end of the suspension ligament 23 is connected to a contralateral side-surface of the lamina 111 of the upper vertebral segment 11 by means of the washer 22. The suspension ligament 23 is connected between the pedicle anchor 21 and the washer 22, and is thus fixed to the pedicle 122 of the lower vertebral segment 12 and the lamina 111 of the upper vertebral segment 11 by means of the pedicle anchor 21 and the washer 22, respectively. In addition, the suspension ligament 23 is tightened to a predetermined tension, and the upper vertebral segment 11 is suspended by combination of the pedicle anchor 21 and the suspension ligament 23 from the lower vertebral segment 12 below.

In this embodiment, the lamina 111 of the upper vertebral segment 11 is provided with a transverse tunnel 114 penetrating the left and right side-surfaces of the lamina 111. Preferably, the tunnel 114 is formed in a relatively thicker or stronger portion of the lamina 111. The number of the pedicle anchors 21 is two, which are respectively arranged at the two pedicles 122 and 123 of the lower vertebral segment 12. The number of the washers 22 is two, which are respectively located at the left and right ends of the tunnel 114 of the lamina 111 of the upper vertebral segment 11. The number of the suspension ligaments 23 is two; in which, one end of one of the suspension ligaments 23 is fixed to the pedicle anchor 21 located in the left pedicle 122, while the other end of the same suspension ligament 23 is first passed through the tunnel 114 from the left side-surface to the right side-surface of the lamina 111 of the upper vertebral segment 11 and then connected to the washer 22 located at the right side-surface of the lamina 111; on the other side, one end of the other suspension ligament 23 is fixed to the pedicle anchor 21 located in the right pedicle 123, while the other end of this suspension ligament 23 is first passed through the tunnel 114 from the right side-surface to the left side-surface of the lamina 111 of the upper vertebral segment 11 and then connected to the washer 22 located at the left side-surface of the lamina 111.

In a preferred embodiment, the transverse tunnel 114 is created with a 2 mm burr head through a point which is usually located between the upper ¼ to ⅓ of the roof of the lamina 111. The tunnel 114 allows passage of suspension ligaments 23 from both sides to be tightened by suspension pedicle anchors 21 from a segment 12 below. An optimal tension can be achieved as the pedicle anchor 21 is placed further down, the optimal tension can be measured by a tension gauge or felt by the finger of a surgeon. The optimal tension is defined by observing the movement of facet joints of less than 1 mm when the base of lamina 111 of the upper segment 11 was pulled and tested with a towel clip.

In an embodiment, the T-PAS system 20 of the present invention further includes a hollow sleeve 24 plugged in the tunnel 114, and both the suspension ligaments 23 pass through the sleeve 24. Or alternatively, the sleeve 24 may not be provided, but a conventional file or a hand-held file 96 (i.e., Off-Set Burr Hole Tap; see FIG. 15) of the present invention may be used to smooth the inner surface and the edges of both ends of the tunnel 114 on the lamina 111, in order to avoid the sharp edges or rough inner surface of the tunnel 114 of the lamina 111 from cutting the suspension ligament 23, or avoid the edges of the tunnel 114 from being broken due to the high tension and friction of the suspension ligament 23.

In this embodiment, the suspension ligament 23 is artificial ligament; the pedicle anchor 21 is a pedicle screw having external threads; and the washer 22 has a length greater than the diameter (or width) of the tunnel 114, such that the washer 22 can press against the outer side-surface of the tunnel 114 of the lamina 111 and will not fall into the tunnel 114 due to the tension of the suspension ligament 23. The materials of the pedicle anchor 21 and the washer 22 can be made of titanium alloy, or ceramic, or other materials that will not cause allergies or rejection to human body.

Please refer to FIGS. 3A to 3E, which are schematic diagrams respectively showing the steps for installing the T-PAS system of the present invention onto two adjacent vertebral segments.

As shown in FIG. 3A, when the T-PAS system 20 of the present invention is to be installed on two adjacent vertebral segments 11 and 12, a drilling tool 91 is first used to drill a small hole of a predetermined depth in the left pedicle 122 of the lower vertebral segment 12. Then, use a screwdriver 92 (i.e., Pedicle Anchor Driver) to screw and fix the pedicle anchor 21 into the small hole at the pedicle 122, wherein the pedicle anchor 21 is pre-assembled with the suspension ligament 23. At this moment, the suspension ligament 23 connected to the pedicle anchor 21 has no tension and is in a loosened state. And then, as shown in FIG. 3B, the end of the suspension ligament 23 away from the pedicle anchor 21 is moved to pass through the tunnel 114 (or sleeve 24) from the left side-surface to the right side-surface of the lamina 111 of the upper vertebral segment 11, and then is assembled and connected to the washer 22 located at the right side-surface of the lamina 111. At this time, the washer 22 has not yet abutted against the right side-surface of the lamina 111, and the suspension ligament 23 connected between the pedicle anchor 21 and the washer 22 is still in a loosened state. Next, as shown in FIG. 3C, by pulling the suspension ligament 23 from the left side of the lamina 111 toward the left, the washer 22 abuts against the right side-surface of the lamina 111 of the upper vertebral segment 11, and the, after measuring the tension of the suspension ligament 23 with a tension gauge 93 to reach a predetermined tension value, the end of the suspension ligament 23 is fixed and the excess suspension ligament 23 is removed (e.g., cut with scissors). And then, the same steps illustrated in FIG. 3A to FIG. 3C are repeated for installing another set of pedicle anchor, washer and suspension ligament; as shown in FIG. 3C, FIG. 3D and FIG. 3E, the right pedicle 123 of the lower vertebral segment 12 is also screwed with a pedicle anchor 21 which is pre-assembled with a suspension ligament 23 (as shown in FIG. 3C). Then, an end of the suspension ligament 23 is also first passing through the tunnel 114 (or sleeve 24) from the right side-surface to the left side-surface of the lamina 111 of the upper vertebral segment 11 and then connected to the washer 22 located at the left side-surface of the lamina 111 (see FIG. 3D). And then, after the suspension ligament 23 is pulled to reach the predetermined tension value, the end of the suspension ligament 23 is fixed and the excess suspension ligament 23 is removed (as shown in FIG. 3E). With these steps of installing procedure, the installation of the T-PAS system 20 of the present invention can be completed for suspending the upper vertebral segment 11 from the lower vertebral segment 12 below via the combination of the pedicle anchor 21 and the suspension ligament 23. The T-PAS system 20 of the present invention can suspend the upper vertebral segment from the lower vertebral segment through suspension ligaments; it not only can stabilize the structural strength of the spine, but also can reduce the number of pedicle anchors (pedicle screws) required for surgery, shorten the operation time, reduce the risk of nerve injury, reduce bleeding, maintain postoperative vertebral mobility, avoid accelerated degeneration of adjacent segments caused by internal fixation and fusion, reduce postoperative discomfort, ache and stiffness of patient's back, and accelerate the patient's recovery time after the vertebral surgery.

In the aforementioned embodiment, the installation of the pedicle anchor 21 and the suspension ligament 23 on one side (left side) is completed first, and then the steps for installing the other pedicle anchor 21 and the other suspension ligament 23 on the other side (right side) are started. However, in another embodiment of the present invention, the pedicle anchors 21 and suspension ligaments 23 on both sides can also be installed simultaneously. Specifically speaking, the two pedicle anchors 21 located on the left and right pedicles 122 and 123 of the lower vertebral segment 12 can be screwed and fixed to the left and right pedicles 122 and 123 respectively in the same step shown in FIG. 3A; then, the two suspension ligaments 23 connected to the two pedicle anchors 21 are respectively and sequentially having one end thereof passing through the tunnel 114 (or sleeve 24) and extending out of the other side of the lamina 111 of the upper vertebral segment 11 in the step illustrated in FIG. 3B, and then the ends of the two suspension ligaments 23 are respectively assembled with a corresponding washer 22. And then, by pulling the two suspension ligaments 23 separately and sequentially, the two washers 22 are respectively pressed against the two opposite side-surfaces of the lamina 111 of the upper vertebral segment 11; and then, after measuring the tensions of these two suspension ligaments 23 with a tension gauge 93 to reach a predetermined tension value, the ends of these two suspension ligaments 23 are fixed and the excess suspension ligaments 23 are removed as shown in FIG. 3E; such procedure can also complete the installation of the T-PAS system 20 of the present invention in order to suspend the upper vertebral segment 11 from the lower vertebral segment 12 below by using the suspension ligaments 23, washers 22 and pedicle anchors 21.

Figure 4A:
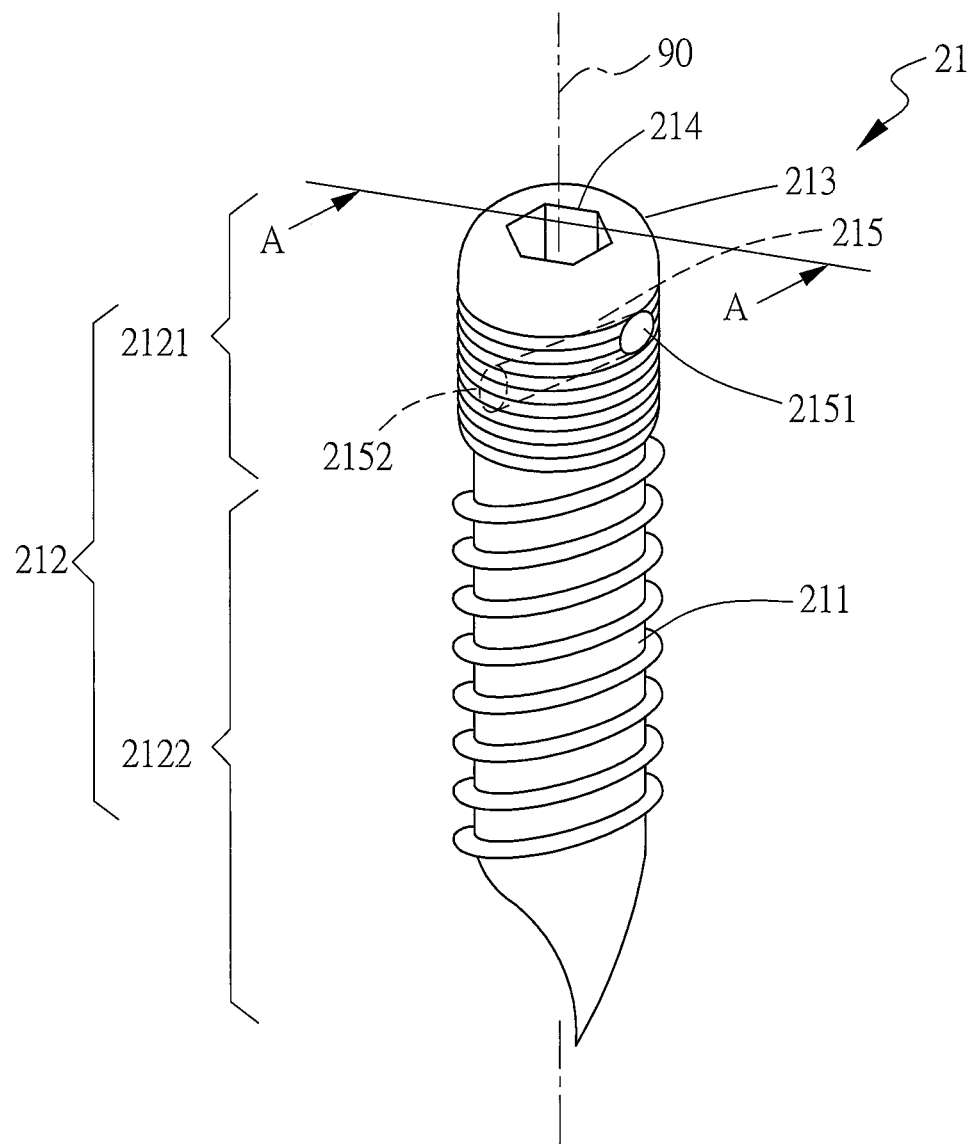
FIG. 4A and FIG. 4B respectively are a three-dimensional (3D) schematic diagram and an A-A cross-sectional schematic view of an embodiment of the pedicle anchor in the T-PAS system of the present invention.
Figure 4B:
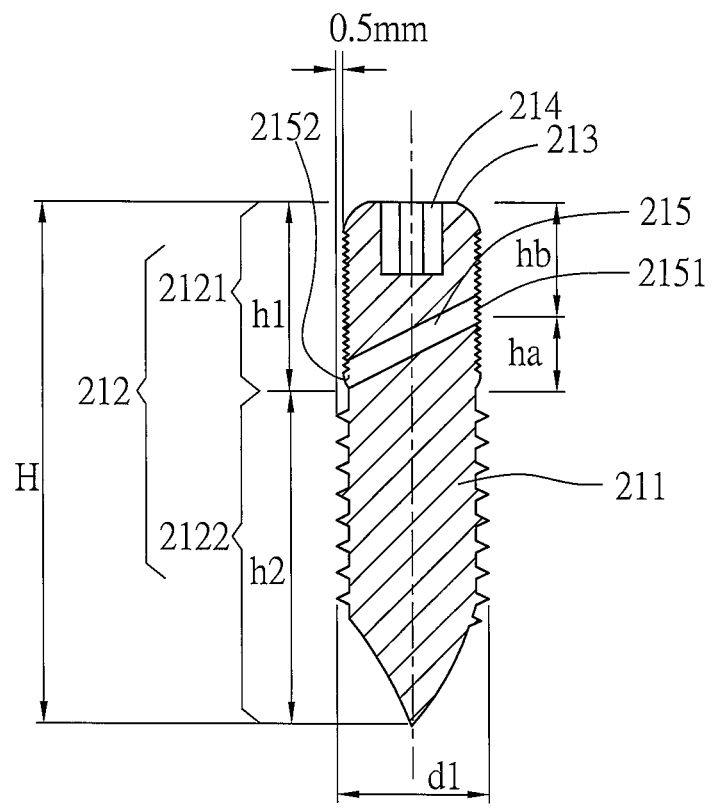

Please refer to FIG. 4A and FIG. 4B, which are respectively a three-dimensional (3D) schematic diagram and an A-A cross-sectional schematic view of an embodiment of the pedicle anchor in the T-PAS system of the present invention. In this embodiment, the pedicle anchor 21 has an elongated and narrow columnar body 211 extending along a central axis 90, an external thread 212 arranged on the outer surface of the columnar body 211, a fitting structure 214 arranged at a top end 213 of the columnar body 211, and an oblique through hole 215 penetrating through the columnar body 211. Wherein, the oblique through hole 215 is not parallel to the central axis; the oblique through hole 215 passes through the central axis 90; the openings at two ends of the through hole 215 are respectively called the upper opening 2151 and the lower opening 2152. The distance "hb" between the upper opening 2151 and the top end 213 of the columnar body 211 is smaller than the distance "ha+hb" between the lower opening 2152 and the top end 213 of the columnar body 211. In other words, the distance between the upper and lower openings 2151 and 2152 along the direction of the central axis 90 is "ha". The oblique through hole 215 allows the suspension ligament 23 to pass through, so that the pedicle anchor 21 is hung on the suspension ligament 23. The fitting structure 214 can be connected with the front end of the screwdriver 92, such that, by operating the screwdriver 92, the pedicle anchor 21 is driven to rotate about the central axis 90, and the pedicle anchor 21 can be screwed and fixed to the pedicle 122. In this embodiment, the fitting structure 214 is a hexagonal recess, whose contour and size are corresponding to the hexagonal post on the front end of the screwdriver 92. The external thread 212 provided on the outer surface of the columnar body 211 of the pedicle anchor 21 includes a smaller-pitched threaded portion 2121 and a larger-pitched threaded portion 2122. The smaller-pitched threaded portion 2121 is disposed closer to the top end 213 of the columnar body 211, and has a relatively lower thread height and smaller thread pitch. The larger-pitched threaded portion 2122 is disposed away from the top end 213 of the columnar body 211, and has a relatively higher thread height and larger thread pitch. In addition, the upper opening 2151 and the lower opening 2152 are both located closer to the top end 213 of the columnar body 211, so the two openings 2151 and 2152 are both located at the smaller-pitched thread portion 2121. In the present invention, several pedicle anchors 21 of different sizes and specifications can be produced in advance in order to adapt to different vertebrae sizes or structures of different patients. Generally speaking, for the pedicle anchors 21 used in the T-PAS system 20 of the present invention, as shown in FIG. 4B, the outer diameter "d1" of the columnar body 211 is between 3.5 mm-6.5 mm, and the total length "H" is between 20 mm-35 mm. In this embodiment, the distance "hb" between the upper opening 2151 and the top end 213 of the columnar body 211 is between 3 mm-7 mm, the distance "ha" between the two openings 2151 and 2152 in the direction of the central axis 90 is between 2 mm-4 mm, the height "h1" of the smaller-pitched thread portion 2121 can be between 5 mm-11 mm, and the height "h2" of the larger-pitched thread portion 2122 can be between 14 mm-30 mm.

In the embodiment shown in FIG. 4A and FIG. 4B, there are two reasons for the external thread 212 of the pedicle anchor 21 to be designed to include a smaller-pitched thread portion 2121 adjacent to the top end 213 of the columnar body 211 and a larger-pitched thread portion 2122 far from the top end 213: (1) the hardness and density of the bone at the pedicle 122 is relatively high near the surface, while the hardness and density of the bone deep inside is relatively low; (2) when the pedicle anchor 21 is screwed into the pedicle 122, the area above the lower opening 2152 of the pedicle anchor 21 (that is, the area between the lower opening 2152 and the top end 213) will be wound by the suspension ligament 23 on the outer surface of the pedicle anchor 21. Therefore, by using a smaller-pitched thread portion 2121 with a smaller thread height and smoother thread tip near the top end 213 of the columnar body 211 of the pedicle anchor 21, not only the probability that the bone surface of the pedicle 122 being damaged by the pedicle anchor 21 can be reduced, the tightness of screw screwing can be improved, and the risk of the suspension ligament 23 being scratched or damaged by the thread of the pedicle anchor 21 can be significantly reduced. However, in another embodiment, the external thread 212 of the pedicle anchor 21 can also be designed such that the thread height and spacing remain the same no matter it is adjacent to or away from the top end 213, only that, the thread tip of the smaller-pitched thread portion 2121 is relative smoother. In a further embodiment, the external thread 212 of the pedicle anchor 21 can also be such designed that: the outer surface of the portion near to the top end 213 of the pedicle anchor 21 (that is, so-called smaller-pitched thread portion 2121) is formed with a rough surface without any thread, while the other portion away from the top end 213 of the pedicle anchor 21 (that is, so-called larger-pitched thread portion 2122) is formed with ordinary larger-pitched and sharp-tipped thread. And in yet a further embodiment, the external thread 212 of the pedicle anchor 21 can also be designed as that: the height of the thread near the top end 213 is relatively low, and the tip of the thread near the top end 213 is relatively smoother, but the pitch thereof remains the same; in contrast, the height and sharpness of the screw thread far from the top end 213 is relatively high, but the pitch remains the same. All such novel designs of the thread of pedicle anchor 21 can achieve the same advantages that: the probability that the bone surface of the pedicle 122 being damaged by the pedicle anchor 21 is reduced, the tightness of screw fixing is improved, and the risk of the suspension ligament 23 being scratched or damaged by the thread of the pedicle anchor 21 is significantly reduced. In a preferred embodiment, the outer diameter of the larger-pitched thread portion 2122 of the columnar body 211 is slightly larger than the outer diameter of the smaller-pitched thread portion 2121 of the columnar body 211 of the pedicle screw 21; such that, a small gap of around 0.5 mm or less is formed due to the difference between the outer diameters of the larger-pitched thread portion 2122 and the smaller-pitched thread portion 2121. Such novel design can minimize the risk to scratch or damage the suspension ligament 23 when the suspension ligament 23 is wound around the outer periphery of the smaller-pitched thread portion 2121 of pedicle anchor 21 which is installed in the pedicle 122.

Figure 5:
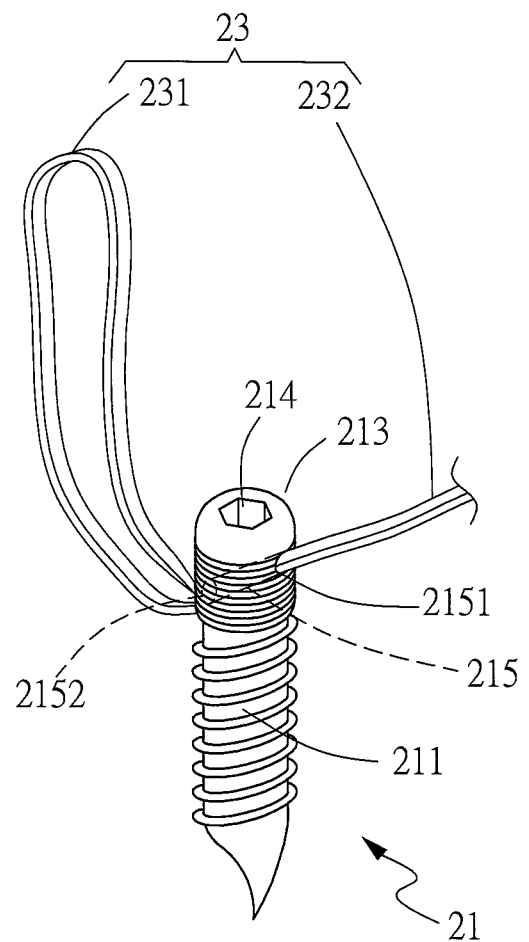
FIG. 5 is a schematic diagram showing an embodiment of the method for assembling the suspension ligament to the pedicle anchor of the T-PAS system of the present invention.

Please refer to FIG. 5, which is a schematic diagram showing an embodiment of the method for assembling the suspension ligament to the pedicle anchor of the T-PAS system of the present invention. In one of the embodiments of the present invention, a middle section of the suspension ligament 23 is folded into a double-line side-by-side structure and has a closed end 231 at the folded section and an open end 232 away from the folded section. The way to pass the suspension ligament 23 through the oblique through hole 215 is to pass the closed end 231 of the folded suspension ligament 23 into the oblique through hole 215 through the upper opening 2151, and then the closed end 231 of the folded suspension ligament 23 is pulled out from the lower opening 2152 of the oblique through hole 215; in the meantime, the open end 232 of the folded suspension ligament 23 remains exposed to the outside of the upper opening 2151.

Figure 6A:
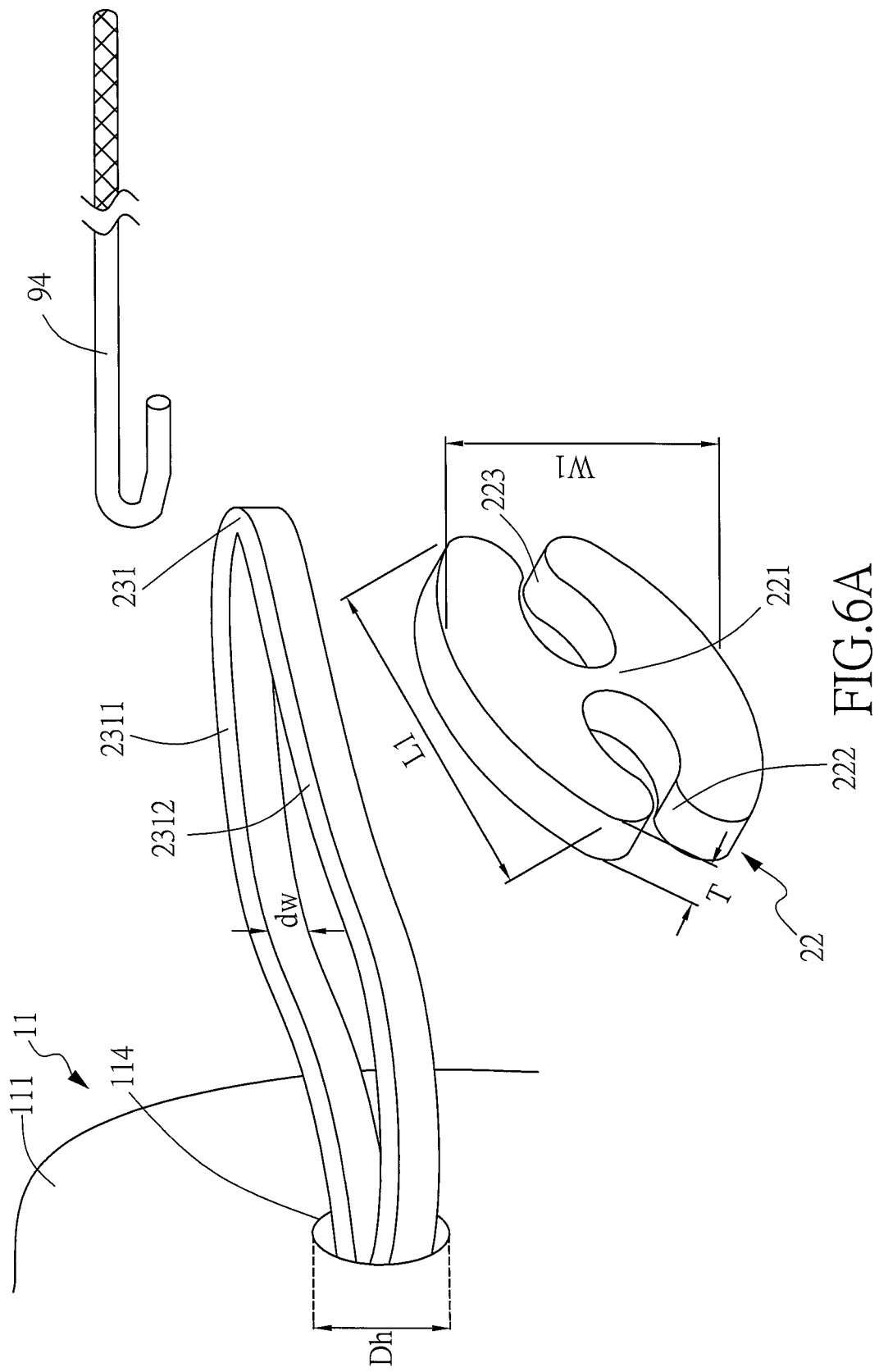
FIG. 6A and FIG. 6B are schematic diagrams showing an embodiment of the two steps for assembling the suspension ligament to the washer of the T-PAS system of the present invention.
Figure 6B:
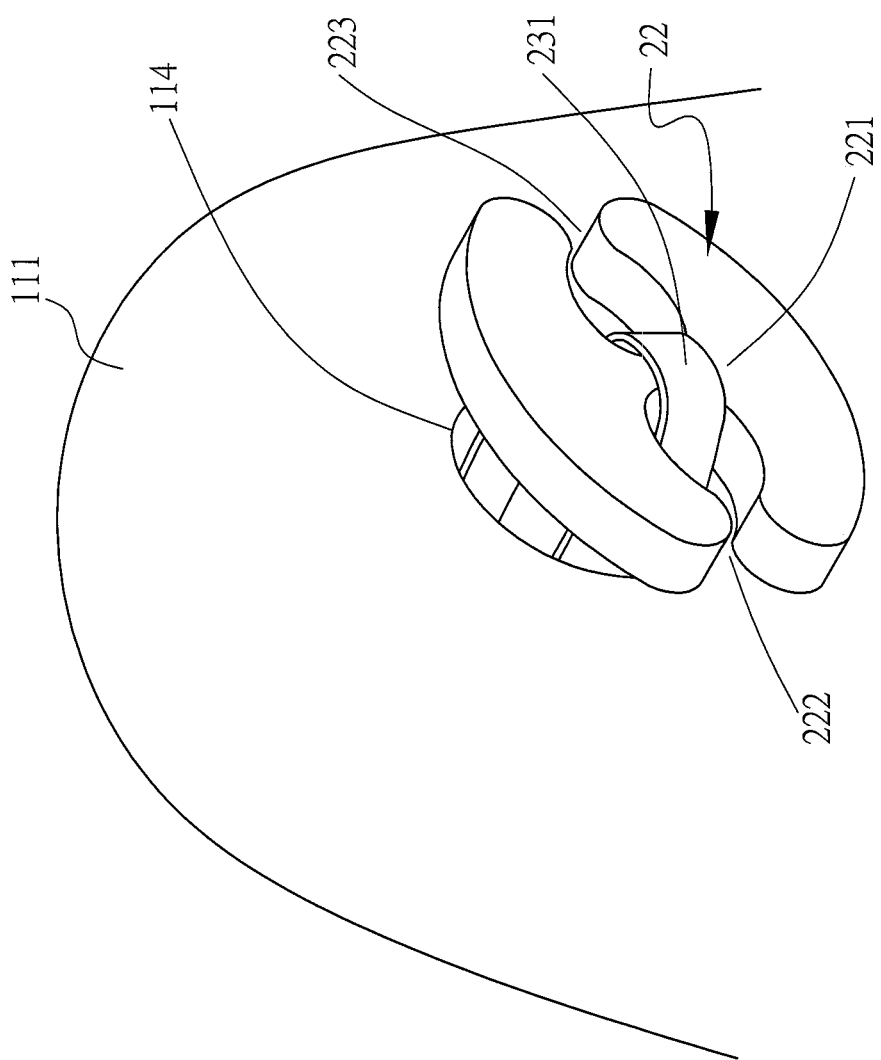

Please refer to FIG. 6A and FIG. 6B, which are schematic diagrams showing an embodiment of the steps for assembling the suspension ligament to the washer of the T-PAS system of the present invention. The washer 22 shown in FIG. 6A and FIG. 6B is an example of the Laminar Pig-Nose Washer. In one of the embodiments of the present invention, the method for assembling the suspension ligament 23 to the washer 22 is to first pull the closed end 231 of the folded middle section of the suspension ligament 23 out of the oblique through hole from the lower opening 2152 of the pedicle anchor 21; and secondly, use a slender elongated hook 94 (i.e., Suspension Ligament Off-Set Passer) to pass through the tunnel 114 of the lamina 111 of the upper vertebral segment from right to left, and use the hook 94 to hook the closed end 231 of the folded suspension ligament 23 on the left side of the lamina 111, and then pull the hook 94 together with the closed end 231 of the folded suspension ligament 23 toward right out of the tunnel 114 of the lamina 111; such that, the closed end 231 of the folded suspension ligament 23 is pulled through the tunnel 114 of the lamina 111 of the upper vertebral segment 11 (as shown in FIG. 6A).

And thirdly, the closed end 231 of the folded suspension ligament 23 is placed on a bar portion 221 of the washer 22. The way to place the suspension ligament 23 onto the washer 22 is that, the left and right line segments 2311, 2312 of the closed end 231 of the suspension ligament 23 are inserted into the washer 22 through the openings 222, 223 on the left and right sides of the washer 22, respectively; so that the closed end 231 of the folded suspension ligament 23 can hook the rod 221 in the middle of the washer 22. After that, a pulling force is applied from the open end (not shown in this figure) of the suspension ligament 23 on the left side of the lamina 111, forcing the washer 22 to press the outer side-surface of the right end of the tunnel 214 of the lamina 111 of the upper vertebral segment 11, so as to achieve the effect of combining and fixing the closed end 231 of the suspension ligament 23 to the lamina 111 of the upper vertebral segment 11 by means of the washer 22 (as shown in FIG. 6B). In this embodiment, the shape of the washer 22 is similar to an "H" structure, and its length "L1" and width "W1" are larger than the diameter "Dh" of the tunnel 214 of the lamina 111, so it can be stuck outside the tunnel 214 and will not fall into the tunnel 214, and thus the closed end of the suspension ligament 23 can be fixed to the lamina 111 as long as the suspension ligament 23 is tightened by a predetermined tension. Preferably, the diameter "Dh" of the tunnel 214 of the lamina 111 can be between 1.5 mm-5 mm, the length "L1" of the washer 22 can be between 6 mm-10 mm, the width "W1" of the washer 22 can be between 6 mm-8 mm, and the thickness "T" of the washer 22 can be between 0.5 mm-2 mm. Preferably, the suspension ligament 23 is a flat strip-shaped artificial ligament, and its width "dw" can be between 1.5 mm-4 mm.

Figure 7A:
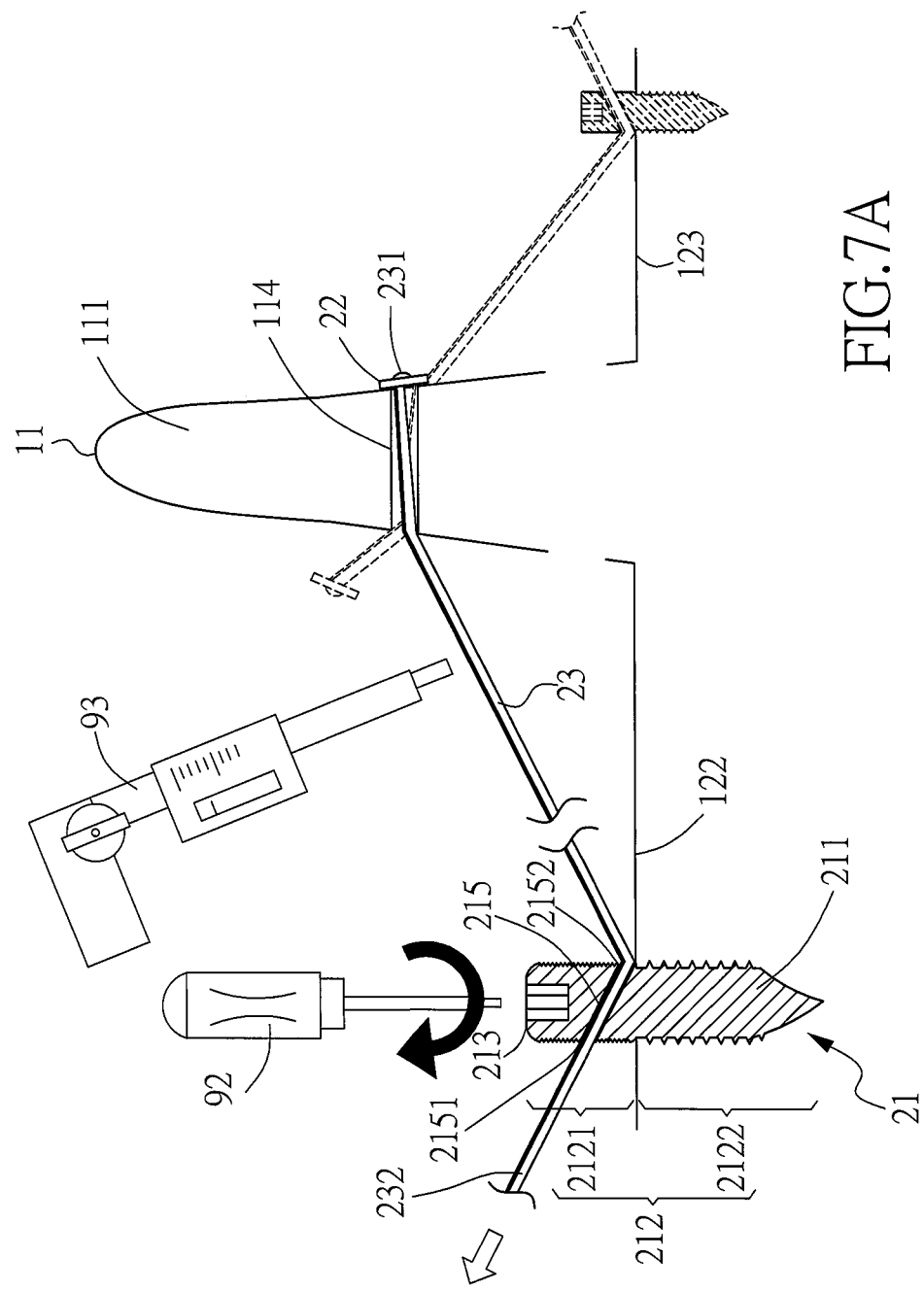
FIG. 7A and FIG. 7B respectively are schematic diagrams showing an embodiment of the steps for fixing the pedicle anchor to the pedicle of the lower vertebral segment in the T-PAS system of the present invention.
Figure 7B:
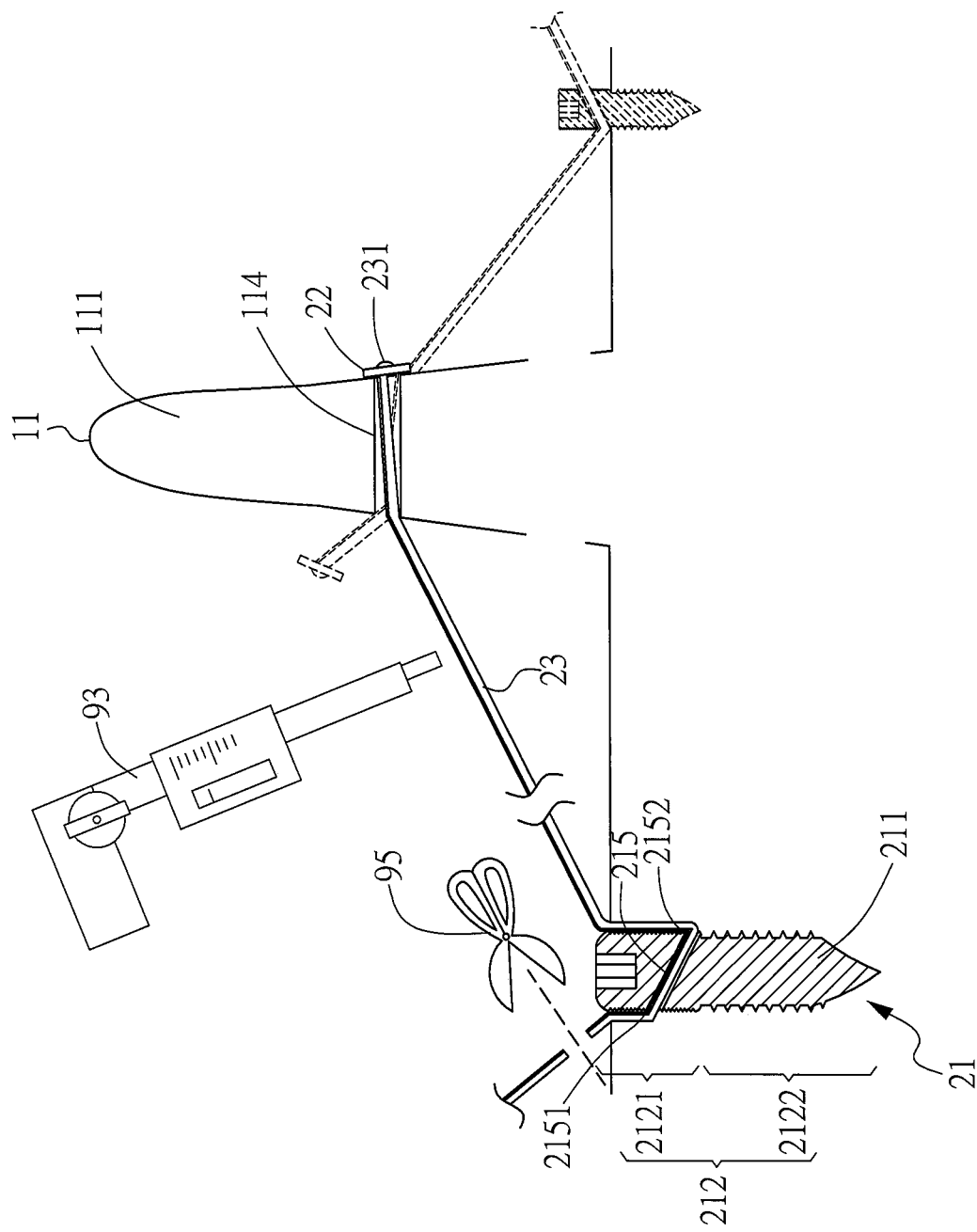

Please refer to FIG. 7A and FIG. 7B, which are respectively a schematic diagram showing an embodiment of the steps for fixing the pedicle anchor to the pedicle of the lower vertebral segment in the T-PAS system of the present invention. In one of the embodiments of the present invention, the method of fixing the pedicle anchor 21 to the pedicle 122 of the lower vertebral segment 12 is to first pull the closed end 231 of the middle section of the folded suspension ligament 23 out of the lower opening 2152 of the oblique through hole 215 of the pedicle anchor 21; then, screw a lower part of the columnar body 211 of the pedicle anchor 21 (for example, the larger-pitched thread portion) into the pedicle 122 of the lower vertebral segment 12, in order to make the lower opening 2152 of the pedicle anchor 21 close to but still exposed on the outer surface of the pedicle 122 of the lower vertebral segment 12 (as shown in FIG. 7A). Then, gently apply a slight pulling force from the open end 232 of the folded suspension ligament 23 so that the suspension ligament 23 temporarily has a relatively small first tension. This first tension must be less than the predetermined tension required by the suspension ligament 23 when the T-PAS system of the present invention is completely installed. The tension value of the suspension ligament 23 can be measured by operating the tension gauge 93 during the process of screwing the anchor 21. And then, when the screwdriver 92 is operated to screw the pedicle anchor 21, the pedicle anchor 21 is gradually screwed into the pedicle 122 of the lower vertebral segment 12, such that the lower opening 2152 of the pedicle anchor 21 is gradually embedded (sunk) into the pedicle 122 of the lower vertebral segment 12, and in the meantime, the suspension ligament 23 is gradually wound around the outer surface of the smaller-pitched thread portion 2121 of the pedicle anchor 21 and thus clamped between the outer surface of the pedicle anchor 21 and the inside of the pedicle 122 of the lower vertebral segment 12 (as shown in FIG. 7B). So that, one end of the suspension ligament 23 is clamped and fixed between the pedicle anchor 21 and the pedicle 122; in the meantime, the other end of the suspension ligament 23 is fixed to the contralateral side-surface of the lamina 111 of the upper vertebral segment 11 by using the washer 22. Thereby, in addition to connecting and fixing one end of the suspension ligament 23 to the pedicle 122 of the lower vertebral segment 12, the suspension ligament 23 can be further pulled by a larger force in order to tighten up the suspension ligament 23 to reach and maintain a relatively larger second tension. The second tension is much greater than the first tension and is the predetermined tension when the T-PAS system is completely installed. When the tension of the suspension ligament 23 measured by the tension gauge 93 has reached the predetermined tension, scissors 95 or surgical knives can be used to cut off the excess suspension ligament 23 (from the open end 232 of the tail of the suspension ligament 23) that is still exposed outside the pedicle 122. Similarly, the other pedicle anchor located on the other side is also screwed into the pedicle 123 in the same way and steps, furthermore, the predetermined tension is also provided to the suspension ligament fixed to the other pedicle anchor. When the operation of screwing the pedicle anchor 21 into the pedicle 122 is completed, the top end 213 of the anchor 21 will only slightly protrude or even be flush with the surface of the pedicle 122. After the T-PAS system 20 of the present invention is installed, only two pedicle anchors 21 need to be screwed into the pedicles 122, 123 of the lower vertebral segment 12, and the top end 213 of each pedicle anchor 21 is either flush with the surface of the pedicle 122 or only slightly protruding beyond the surface of the pedicle 122; generally speaking, the height of the top end 213 of the pedicle anchor 21 protruding beyond the surface of the pedicle 122 will not be higher than 5 mm. In addition, the washer 22 is also a thin-plate structure and is attaching on the side-surface of the lamina, such that the patient won't feel uncomfortable or foreign body sensation. Moreover, the suspension ligament 23 composed of artificial ligaments will not cause discomfort or pain to the patient, which does improve all the shortcomings of conventional technologies.

The aforementioned embodiment is merely one of preferred embodiments of the T-PAS system of the present invention, and not the only applicable embodiment. In the present invention, the structures of the pedicle anchor and the washer are not limited to the structures disclosed above, but there are other implementable structures.

Figure 8:
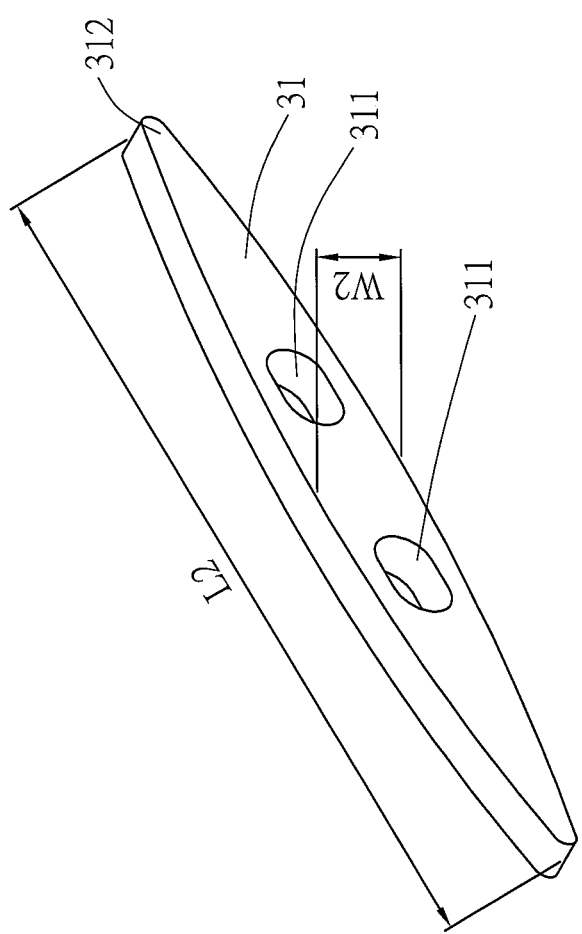
FIG. 8 is a perspective diagram of another embodiment of the washer in the T-PAS system of the present invention.
Figure 9A:
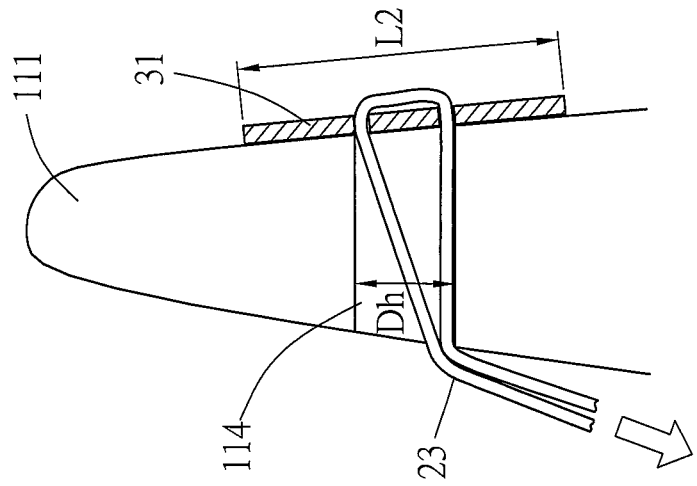
FIG. 9A and FIG. 9B are schematic diagrams of the two steps of the method for connecting the suspension ligament to the washer as shown in FIG. 8 respectively.
Figure 9B:
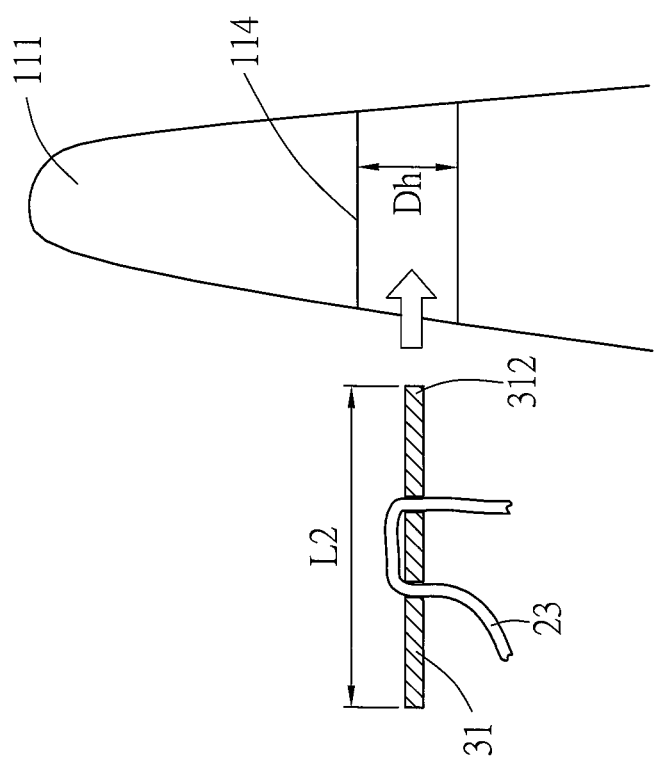

For example, please refer to FIG. 8, FIG. 9A and FIG. 9B; wherein, FIG. 8 is a perspective diagram of another embodiment of the washer in the T-PAS system of the present invention; FIG. 9A and FIG. 9B are schematic diagrams of the two steps of the method for connecting the suspension ligament to the washer as shown in FIG. 8 respectively. The washer 31 shown in FIG. 8 is an example of Laminar Banana Washer. In this embodiment, the washer 31 may be a thin and elongated plate-like structure with a relatively small width "W2" and a relatively long length "L2". The width "W2" of the washer 31 is smaller than the diameter "Dh" of the tunnel 114 of the lamina 111 (W2<Dh), the thickness of the washer 31 is also smaller than the diameter "Dh" of the tunnel 114, and the length "L2" is greater than the diameter "Dh" of the tunnel 114 of the lamina 111 (L2>Dh). Two or more through holes 311 are provided on the washer 31, such that the suspension ligament 23 can be sequentially passed through these through holes 311 to achieve the purpose of binding/assembling the suspension ligament 23 to the washer 31. Next, as shown in FIG. 9A, align the end 312 of the washer 31 connected with the suspension ligament 23 to the tunnel 114 of the lamina 111 in the elongated direction. Utilizing the characteristic that the width "W2" and thickness of the washer 31 are both smaller than the diameter "Dh" of the tunnel 114, the washer 31 together with the suspension ligament 23 can be inserted and then passed through the tunnel 114 of the lamina 111 to the other side of the lamina 111. After that, as shown in FIG. 9B, turn the washer 31 to an angle and pull the suspension ligament 23 from the left side of the lamina 111, then the slender side of the washer 31 with a length of "L2" can press against the right side-surface of the lamina 111, so as to achieve the purpose of fixing one end of the suspension ligament 23 on the right side of the tunnel 114 of the lamina 111 by means of the washer 31.

Figure 10A:
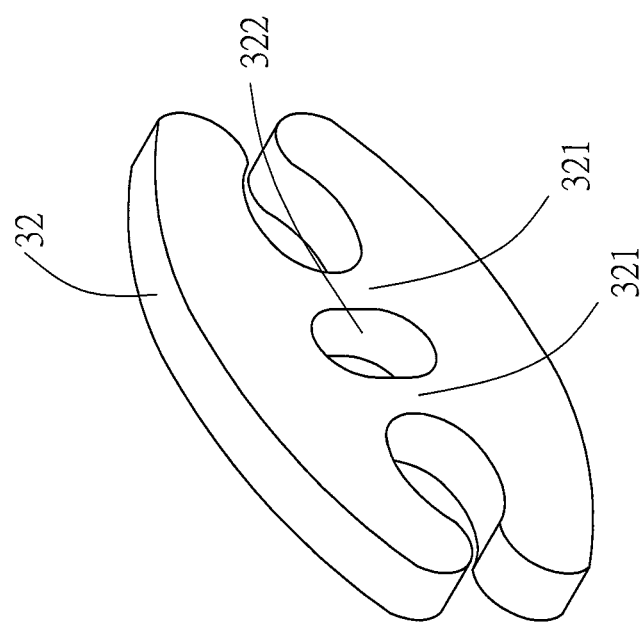
FIG. 10A is a perspective view of yet another embodiment of the washer of the T-PAS system of the present invention.

Please refer to FIG. 10A, which is a perspective view of yet another embodiment of the washer of the T-PAS system of the present invention. The structure of the washer shown in this embodiment is almost the same as the washer shown in FIG. 6A, and the way to use is also similar. The only difference between these two washers is that, the washer 32 shown in FIG. 10A is provided with two bar portions 321, and an additional opening 322 is formed between the two bar portions 321. Such structure allows the suspension ligament to pass through the opening 322 and be wound around the two bar portions 321 of the washer 32, in order to provide a more stable and non-slip binding effect.

Figure 10B:
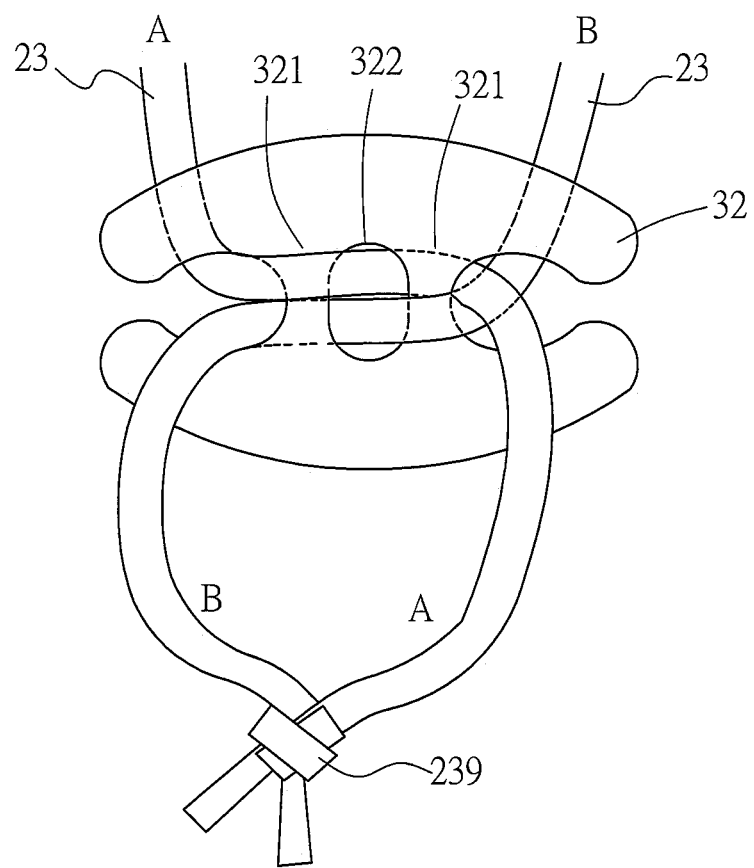
FIG. 10B is a schematic diagram showing an embodiment of a method to tie the suspension ligament on the washer shown in FIG. 10A of the T-PAS system of the present invention.

Please refer to FIG. 10B, which is a schematic diagram showing an embodiment of a method to tie the suspension ligament on the washer shown in FIG. 10A of the T-PAS system of the present invention. In this embodiment, the suspension ligament 23 first passes through the through hole of the pedicle screw (not shown in this figure) such that the pedicle screw is substantially hung on a middle portion of the suspension ligament 23. Then, the free ends of the two strips "A" and "B" of the suspension ligament 23 pass through the tunnel of the lamina (not shown in this figure). After that, the free ends of the two strips "A" and "B" of the suspension ligament 23 pass across the bar portions 321 and the middle opening 322 from two sides of the washer 32 and then are tied up with at least 5 knots 239 to ensure the stability of connection between the suspension ligament 23 and the washer 32.

Figure 11A:
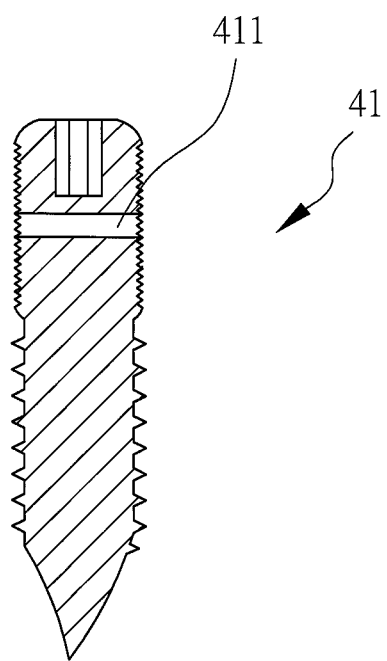
FIG. 11A is a schematic cross-sectional diagram of another embodiment of the pedicle anchor in the T-PAS system of the present invention.

Please refer to FIG. 11A, which is a schematic cross-sectional diagram of another embodiment of the pedicle anchor in the T-PAS system of the present invention. The structure of the pedicle anchor 41 shown in this embodiment is substantially the same as that of the pedicle anchor 21 shown in FIG. 4A and FIG. 4B, and the method of use is also similar. The only difference between these two pedicle anchors is that, the through hole 411 of the anchor 41 shown in FIG. 11A is a horizontal through hole 411, the openings at both ends of the through hole 411 are located at the same height. In the other hand, the two openings 2151, 2152 at two ends of the oblique through hole 215 of the pedicle anchor 21 shown in FIG. 4A and FIG. 4B are located at different heights.

Figure 11B:
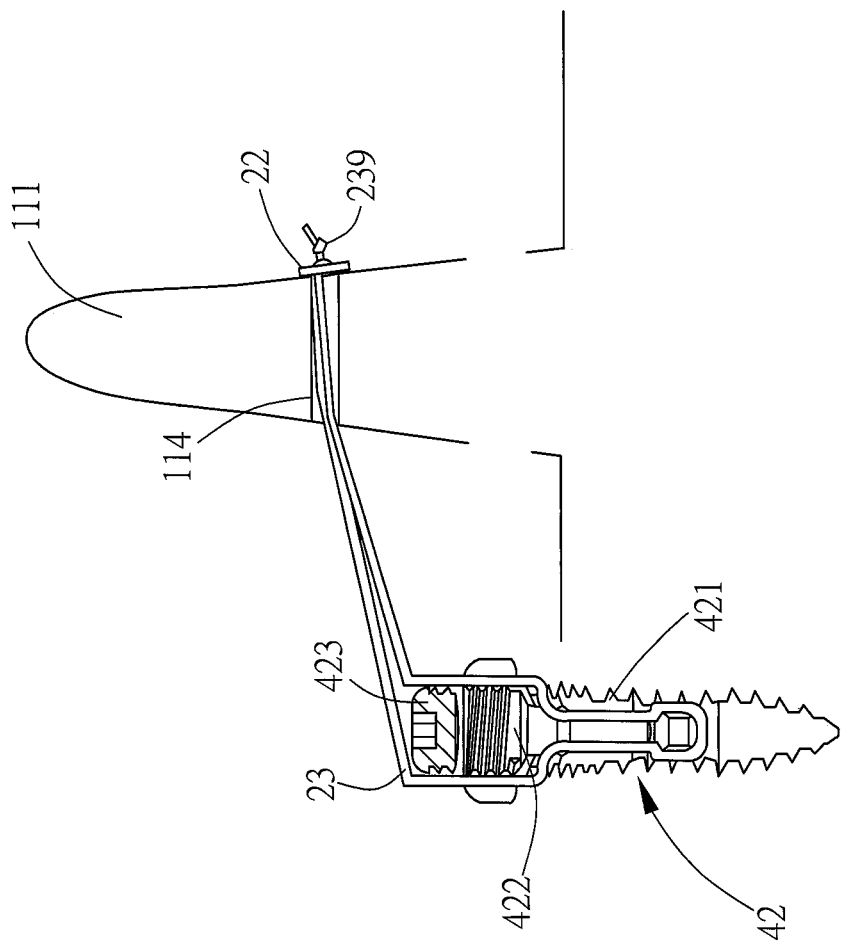
FIG. 11B is a schematic cross-sectional diagram of yet another embodiment of the pedicle anchor of the T-PAS system of the present invention.

Please refer to FIG. 11B, which is a schematic cross-sectional diagram of yet another embodiment of the pedicle anchor of the T-PAS system of the present invention. In this embodiment, the columnar body 421 of the pedicle anchor 42 is provided with a counterbore 422 extending downward from its top end along the direction of the central axis. An internal thread is provided inside the counterbore 422 at an area near the top of the counterbore 422. The closed end of the suspension ligament 23 can be inserted into the counterbore 422 from the top of the columnar body 421; and then, by rotating a cap 423 with external thread from the top of the columnar body 421 into the counterbore 422, the closed end of the suspension ligament 23 can be clamped and fixed between the cap 423 and the counterbore 422 of the columnar body 421, in order to achieve the purpose of assembling and fixing the suspension ligament 23 to the pedicle anchor 42. In this embodiment, since the suspension ligament 23 passes through the tunnel 114 of the lamina 111 with its tail open end, therefore, the method for connecting the suspension ligament 23 to the washer 22 is to tie the suspension ligament 23 to the bar portion of the washer 22, and at least 5 knots 239 are required to ensure the stability of the connection.

Figure 11C:
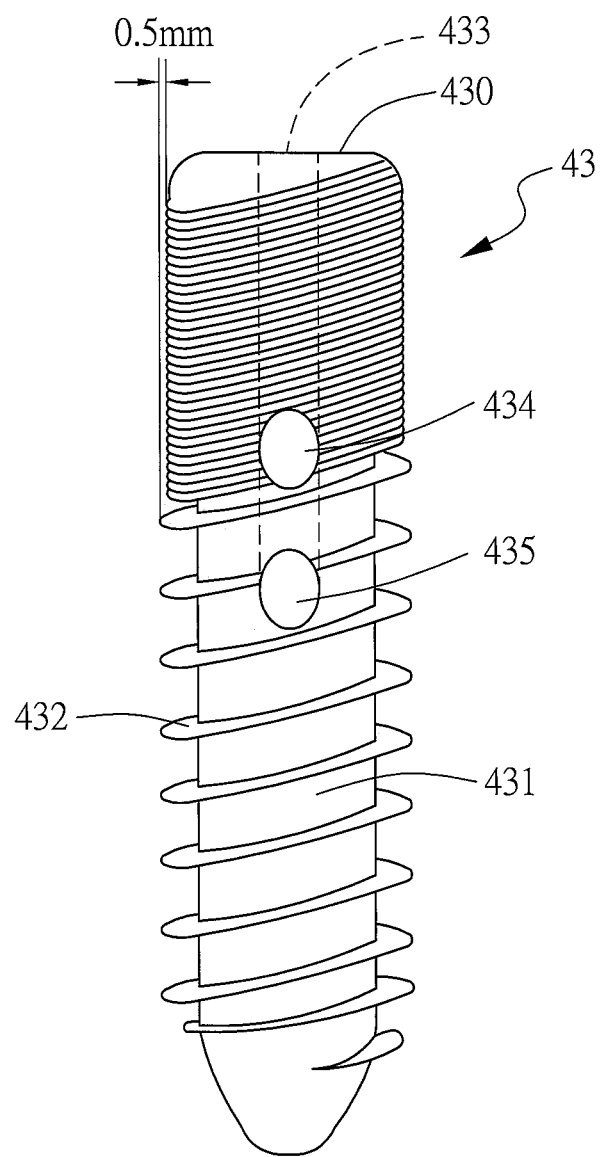
FIG. 11C is a schematic cross-sectional diagram of a further embodiment of the pedicle anchor in the T-PAS system of the present invention.

Please refer to FIG. 11C, which is a schematic cross-sectional diagram of a further embodiment of the pedicle anchor in the T-PAS system of the present invention. In this embodiment, the pedicle anchor 43 also has a columnar body 431 and a counterbore 433 extending downward from the top end 430 of the columnar body 431 along the central axis. Two or more transverse through holes 434, 435 are provided on the columnar body 431, which are connected with the counterbore 433. After the suspension ligament is inserted into the counterbore 433 from the top end 430 of the columnar body 431, the suspension ligament located inside the counterbore 433 can be pulled out of the columnar body 431 from one of the through holes 434 and then inserted into the counterbore 433 again via the other through hole 435, such that the suspension ligament can be bound to the pedicle anchor 43 more firmly. In addition, the pitch and height of the external thread 432 provided on the outer surface of the columnar body 431 are consistent throughout the whole columnar body 431, and there is no difference between the so-called smaller-pitched thread portion or the larger-pitched thread portion.

Figure 11E:
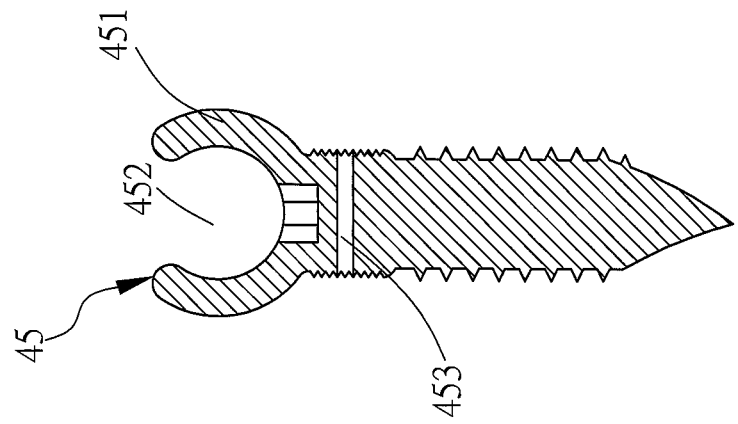
FIG. 11E is a schematic cross-sectional diagram of still another embodiment of the pedicle anchor in the T-PAS system of the present invention.
Figure 11D:
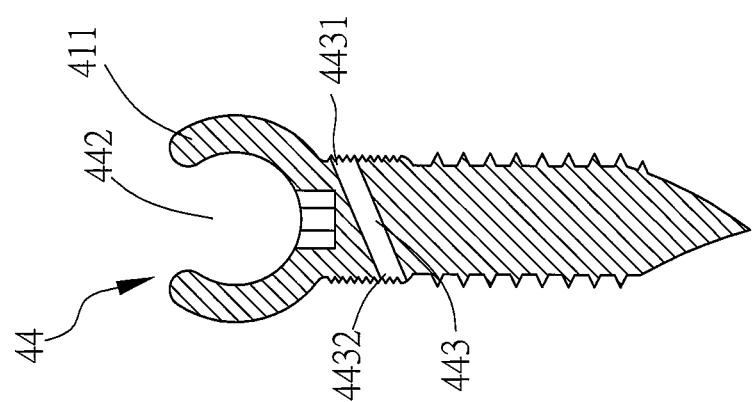
FIG. 11D is a schematic cross-sectional diagram of yet an even further embodiment of the pedicle anchor in the T-PAS system of the present invention.

Please refer to FIG. 11D, which is a schematic cross-sectional diagram of yet an even further embodiment of the pedicle anchor in the T-PAS system of the present invention. The structure of the pedicle anchor 44 shown in this embodiment is substantially the same as that of the pedicle anchor 21 shown in FIG. 4A and FIG. 4B, and the method of use is also similar. In the embodiment shown in FIG. 11D, the pedicle anchor 44 also has an elongated columnar body extending along a central axis, an external thread provided on the outer surface of the columnar body, a fitting structure provided at the top end of the columnar body, and an oblique through hole 443 penetrating columnar body; wherein, the upper opening 4431 and the lower opening 4432 at two ends of the oblique through hole 443 are also located at different height. That means, there is a height difference between the upper opening 4431 and the lower opening 4432 at two ends of the oblique through hole 443. The only difference between the two embodiments shown in FIG. 11D and FIG. 4A is that, a U-shaped rod-holding rack 441 is additionally provided at the top end of the columnar body of the pedicle anchor 44 shown in FIG. 11D. The rod-holding rack 441 has a rod-holding seat 442 for accommodating a connecting rod (not shown in the figure), so that the T-PAS system of the present invention can be used with a conventional spinal fixator.

Please refer to FIG. 11E, which is a schematic cross-sectional diagram of still another embodiment of the pedicle anchor in the T-PAS system of the present invention. The structure of the pedicle anchor 45 shown in this embodiment is substantially the same as that of the pedicle anchor 44 shown in FIG. 11D, and the method of use is also similar. The pedicle anchor 45 also has a U-shaped rod-holding rack 451 and a rod-holding seat 452 at the top end of the columnar body of the pedicle anchor 45. The only difference between the two pedicle anchors 44, 45 is that, the through hole 453 of the pedicle anchor 45 shown in FIG. 11E is a horizontal through hole 453, and the two openings of the two ends of the through hole 453 are located at the same height. In the other hand, the two openings 2151, 2152, 4431, 4432 at two ends of the oblique through hole 215, 443 of the pedicle anchor 21, 44 shown in FIG. 4A, FIG. 4B or FIG. 11D are located at different heights. The pedicle anchors 44 and 45 shown in FIG. 11D and FIG. 11E are two examples of Headed Suspension Pedicle Anchor (HSPA), in which, the U-shaped rod-holding rack 451 (or 441) of the pedicle anchor 45 (or 44) can be a fixed head or a polyaxial head.

When manufacturing or selling the T-PAS system of the present invention, the tools and components required in the T-PAS system can be pre-sterilized, pre-semi-assembled and pre-packaged into a component set, in order to facilitate surgeons in performing surgery that installs the T-PAS system into the patient's vertebrae. In an embodiment, the component set of the T-PAS system of the present invention may include: several pedicle anchors, several washers, several suspension ligaments, a screwdriver, and a tension gauge. The pedicle anchor is used to be fixed to the pedicle of the lower vertebral segment. The washer is located at the end of the tunnel formed in the lamina of the upper vertebral segment. The suspension ligament is used to connect the pedicle anchor and the washer; in addition, the suspension ligament is fixed to both the pedicle of the lower vertebral segment and the lamina of the upper vertebral segment by means of the pedicle anchor and the washer. Moreover, in this component set, the suspension ligament is pre-assembled on the pedicle anchor. The screwdriver can be connected to the pedicle anchor, such that the pedicle anchor can be screwed into the pedicle of the lower vertebral segment by operating the screwdriver. The tension gauge is used to measure the tension of the suspension ligament. With this component set, the process for surgeons to perform surgery for installing the T-PAS system can be facilitated and sped up, thereby reducing the risk of surgery.

Figure 12A:
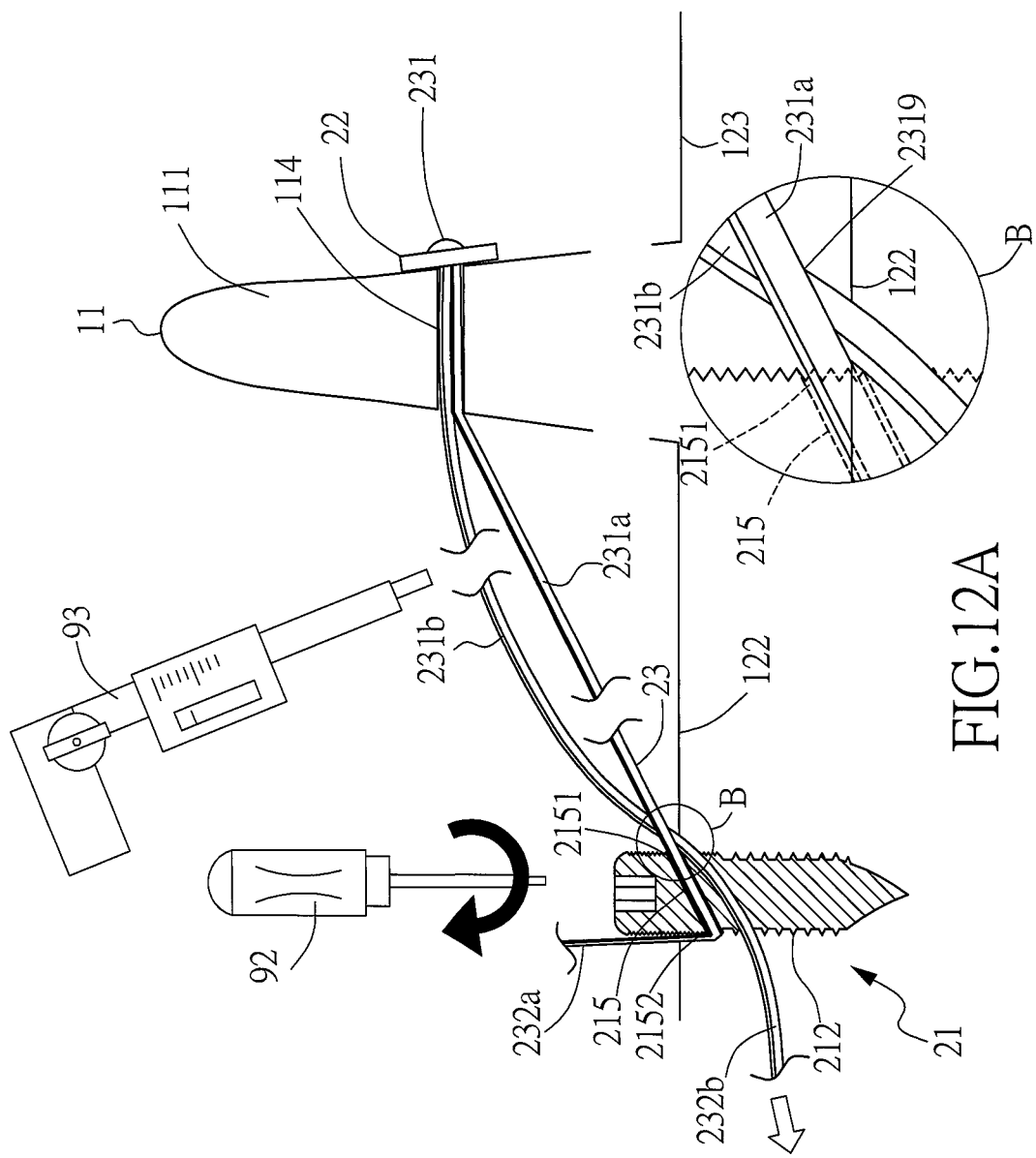
FIG. 12A and FIG. 12B respectively are schematic diagrams showing another embodiment of the steps for fixing the pedicle anchor to the pedicle of the lower vertebral segment in the T-PAS system of the present invention.
Figure 12B:
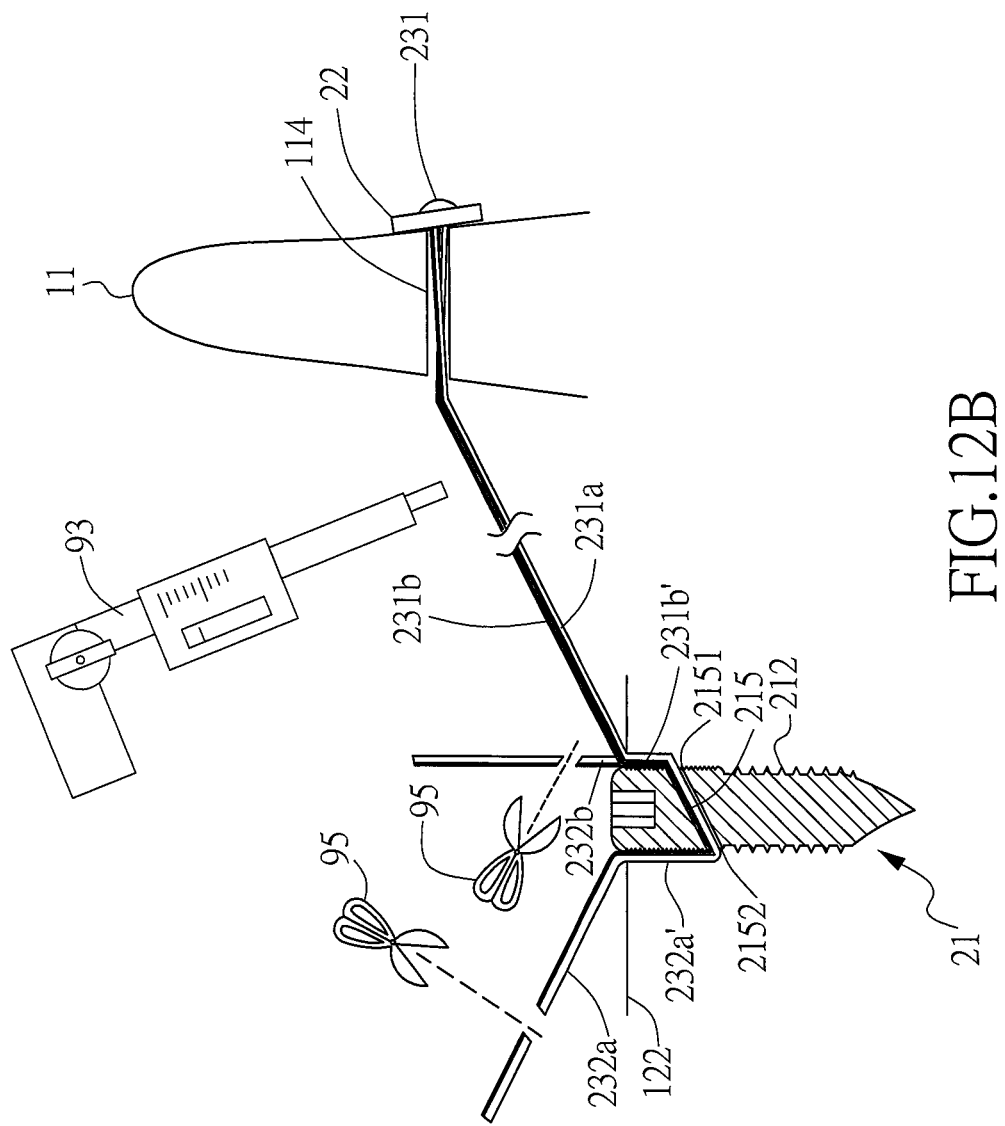

Please refer to FIG. 12A and FIG. 12B, which are respectively a schematic diagram showing another embodiment of the steps for fixing the pedicle anchor to the pedicle of the lower vertebral segment in the T-PAS system of the present invention. In the T-PAS system of the present invention, in addition to the method and steps illustrated in FIG. 7A and FIG. 7B and their related descriptions, the method and steps shown in FIG. 12A and FIG. 12B can also be used to fix the pedicle anchor to the pedicle of the lower vertebral segment. In the embodiment shown in FIG. 12A and FIG. 12B, the way to pass the suspension ligament 23 through the oblique through hole 215 of the pedicle anchor 21 is to pass one end of the suspension ligament 23 through the lower opening 2152 into the oblique through hole 215 and then pull out the suspension ligament 23 out of the oblique through hole 215 via the upper opening 2151, such that the two free ends 232a, 232b (open ends) of the suspension ligament 23 are respectively exposed out of the lower opening 2152 and the upper opening 2151. Wherein, the middle section and the closed end 231 of the suspension ligament 23 are both located at the portion of the suspension ligament 23 pulled out from the upper opening 2151. As shown in FIG. 12A, the method for fixing the pedicle anchor 21 to the pedicle 122 of the lower vertebral segment is to use a screwdriver 92 to first screw a lower part of the pedicle anchor 21 into the pedicle 122 of the lower vertebral segment, such that the lower opening 2152 together with the free end 232a (open end) of the suspension ligament 23 extended out from the lower opening 2152 are screwed into and clamped between the outer surface of the pedicle anchor 21 and the pedicle 122 of the lower vertebral segment; however, in the meantime, the upper opening 2151 and the parts 231a, 231b of the suspension ligament 23 extending out from the upper opening 2151 are still exposed outside the pedicle 122 of the lower vertebral segment. Next, the other free end 232b (open end) of the suspension ligament 23 exposed outside of the pedicle 122 is first pulled to a location near the upper opening 2151, then the other free end 232b (open end) is pulled to pass through the part 231a of the suspension ligament 23 from below, and then, keep pulling the other free end 232b (open end) with a pulling force so that the suspension ligament temporarily has a relatively small first tension. That is, as shown in the partially enlarged view of the upper opening 2151 shown in the lower right area "B" in FIG. 12A, the touched point 2319 of the two parts 231a, 231b of the suspension ligament 23 is exactly stuck at the intersection of the upper opening 2151 and the outer surface of the pedicle 122, and the part 231a is in contact with and pressed against the other part 231b of the suspension ligament 23. And then, as shown in FIG. 12B, use a screwdriver 92 to gradually screw the pedicle anchor 21 into the pedicle 122 of the lower vertebral segment, so that the upper opening 2151 of the pedicle anchor 21 is embedded into the pedicle 122 of the lower vertebral segment; in the same time, the part 231a of the suspension ligament 23 extending from the upper opening 2151 and the other part 231b' connected to the other free end 232b (open end) are both wound around the outer surface of the pedicle anchor 21 and thereby sandwiched and clamped between the outer surface of the pedicle anchor 21 and the inside of the pedicle 122 of the lower vertebral segment. The screwdriver 92 keeps gradually screwing the pedicle anchor 21 into the pedicle 122 to tighten the suspension ligament 23 until the tension of the two parts 231a, 231b of the suspension ligament 23 measured by the tension gauge 93 reaches a relatively large second tension value. In addition to the two free ends 232a, 232b (open ends) of the suspension ligament 23 can be connected and fixed at the pedicle 122 of the lower vertebral segment, the suspension ligament 23 can be further pulled to reach and maintain at a relatively large second tension. The second tension is much greater than the first tension and is the predetermined tension when the T-PAS system is completely installed. When the tension of the suspension ligament 23 measured by the tension gauge 93 has reached the predetermined tension, scissors 95 or surgical knives can be used to cut off the excess suspension ligament 23 from the free ends 232a, 232b (open ends) of the suspension ligament 23. In an embodiment, when the other part 231b of the suspension ligament 23 is passed under the part 231a of the suspension ligament 23 at the upper opening 2151, the other part 231b of the suspension ligament 23 can be additionally wound around the outer surface of the pedicle anchor 21 for one circle or two circles, in order to ensure that, when the pedicle anchor 21 is gradually screwed into the pedicle 122 of the lower vertebral segment by using the screwdriver 92, the other part 231b' will be wound together on the outer surface of the pedicle anchor 21 and thus clamped between the outer surface of the pedicle anchor 21 and the inside of the pedicle 122 of the lower vertebral segment.

Figure 13A:
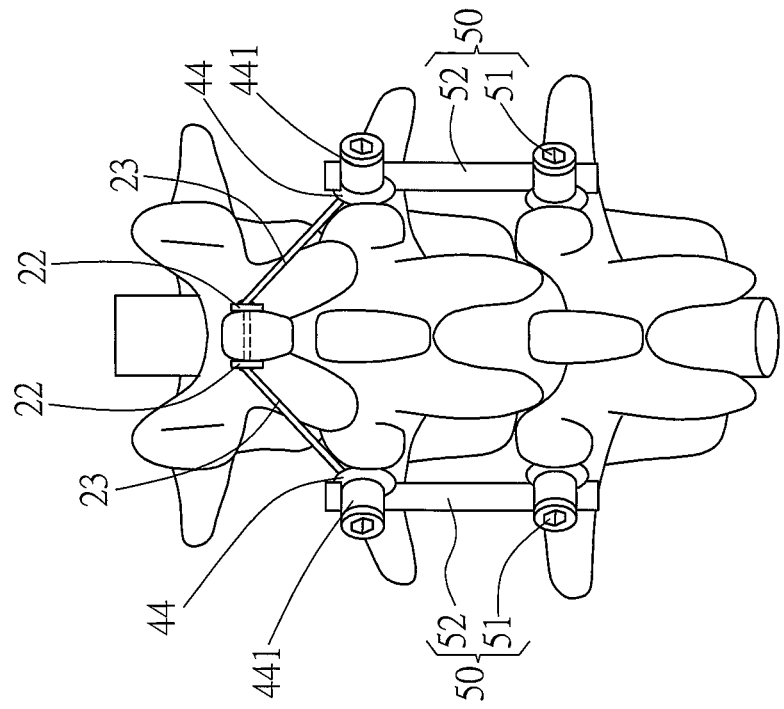
FIG. 13A and FIG. 13B are schematic diagrams of two embodiments of the T-PAS system of the present invention being used with the conventional spinal fixator.
Figure 13B:
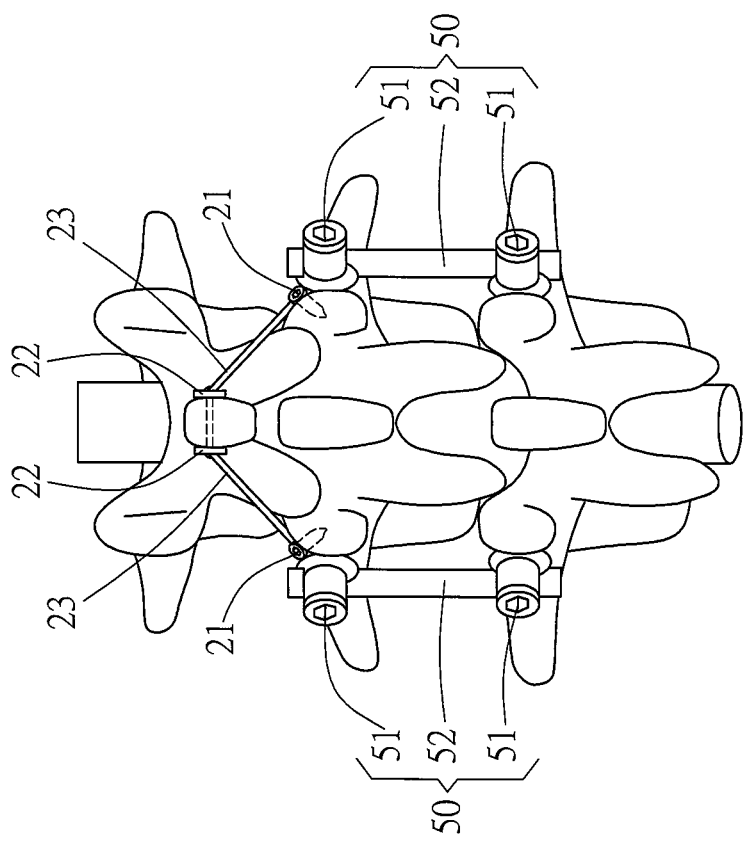

Please refer to FIG. 13A and FIG. 13B, which are schematic diagrams of two embodiments of the T-PAS system of the present invention being used with the conventional spinal fixator. Even if the patient to be operated has already had surgery and installed a conventional spinal fixator before, and now there is a need for spine surgery again, the T-PAS system of the present invention can still be installed in subsequent operations to be used in conjunction with the priorly installed conventional spinal fixator. As shown in FIG. 13A, generally speaking, a typical conventional spinal fixator 50 will include at least four pedicle screws 51 and two connecting rods 52 (fusion rods); wherein, each of the pedicles of both sides of both the upper and lower vertebral segments is screwed with a pedicle screw 51; and then, each pair of the two pedicle screws 51 located on the same side of the upper and lower vertebral segments is connected by a connecting rod 52. Sometimes, a fixing plate (not shown in the figure) is added to the two connecting rods 52 or the pedicle screws 51 to strengthen the fixing effect. In the embodiment shown in FIG. 13A, the T-PAS system of the present invention can select two smaller pedicle anchors 21 of the invention to be respectively screwed on the pedicles of the upper vertebral segment at locations adjacent to (but not contact with) the pedicle screws 51 of the conventional spinal fixator 50. In addition, the two ends of the tunnel of the lamina of a further upper vertebral segment are respectively provided with washers 22 of the T-PAS system of the present invention. Moreover, a suspension ligament 23 with a predetermined tension is used to connect the pedicle anchor 21 on one side and the washer 22 on the other side through the tunnel of the lamina. Thereby, under the premise that the function of the existing conventional spinal fixator 50 is not affected, the T-PAS system of the present invention can be installed between the upper vertebral segment and the further upper vertebral segment in order to suspend them. Wherein, the smaller pedicle anchor 21 used in this embodiment is an example of Suspension Abutment Pedicle Anchor (SAPA).

As shown in FIG. 13B, another way to use the T-PAS system of the present invention conjunction with the conventional spinal fixator 50 is to remove both the left and right conventional pedicle screws of the conventional spine fixator 50 located at the upper vertebral segment; and then replace these two conventional pedicle screws with two pedicle anchors 44 (or 45) equipped with U-shaped rod-holding rack 441 (or 451), rod-holding seat 442 (or 452) and through hole 443 (or 453) as shown in FIG. 11D (or FIG. 11E). In addition, the two ends of the tunnel of the lamina of the further upper vertebral segment are respectively provided with washers 22 of the T-PAS system of the present invention. Moreover, a suspension ligament 23 with a predetermined tension is used to connect the pedicle anchor 44 (or 45) on one side and the washer 22 on the other side through the tunnel of the lamina. Because the pedicle anchor 44 (or 45) of the present invention located in the upper vertebrae also has the rod-holding rack 441 (or 451) and rod-holding seat 442 (or 452), therefore the connecting rod 52 of the conventional spinal fixator 50 that is originally installed can be directly assembled and fixed to the pedicle anchor 44 (or 45) of the present invention. Thereby, under the premise that the function of the existing conventional spinal fixator 50 is not affected, the T-PAS system of the present invention can be installed between the upper vertebral segment and the further upper vertebral segment in order to suspend them. Wherein, the pedicle anchor 44 (or 45) used in this embodiment is an example of Headed Suspension Pedicle Anchor (HSPA).

Figure 14:
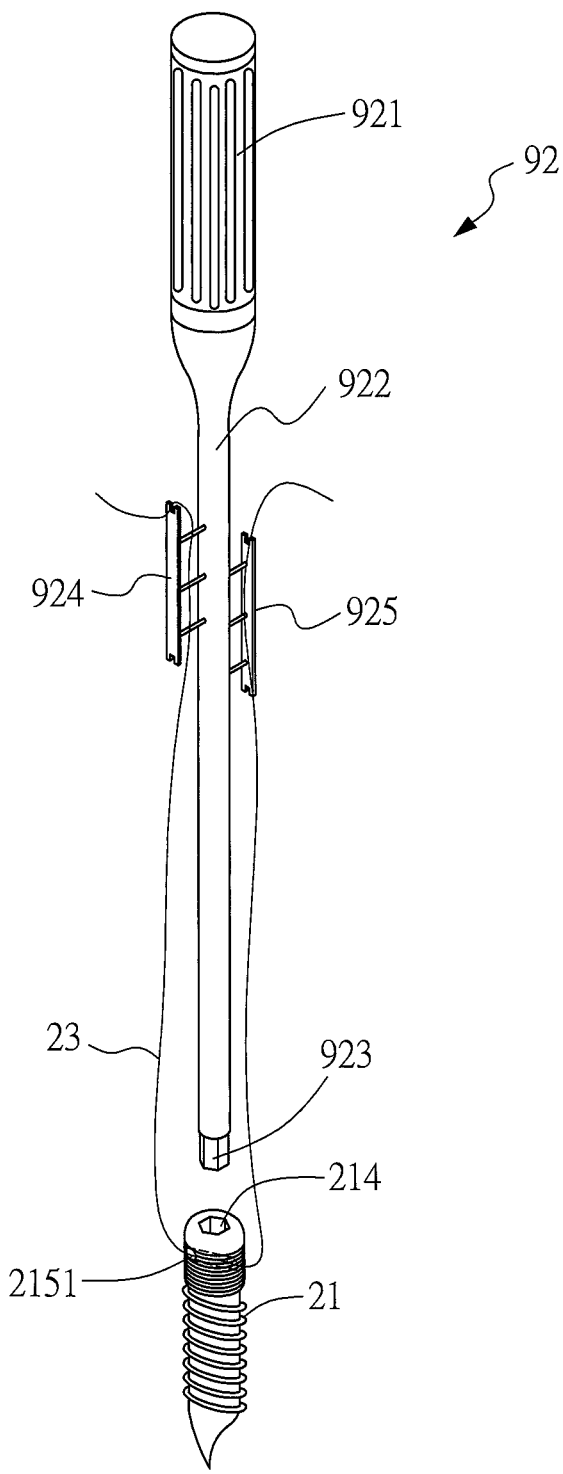
FIG. 14 is a schematic diagram of an embodiment of the screwdriver in the component set of the T-PAS system of the present invention.

Please refer to FIG. 14, which is a schematic diagram of an embodiment of the screwdriver in the component set of the T-PAS system of the present invention. Because the T-PAS system of the present invention uses a slender, long, soft and tough artificial ligament as a suspension wire, in order to prevent the suspension ligament from being entangled by itself or entangled on the screwdriver during the operation, the present invention discloses an innovative screwdriver 92 to overcome the aforementioned problems. As shown in FIG. 14, the screwdriver 92 includes: a handle 921, a long-rod portion 922, a driver head 923, an upper hanger 924 and a lower hanger 925. The long-rod portion 922 extends a predetermined length from one end of the handle 921 along an axis. The driver head 923 is located at an end of the long-rod portion 922 away from the handle 921. The structure of the driver head 923 corresponds to the fitting structure 214 of the pedicle anchor 21 of the present invention and can be connected with the fitting structure 214 of the pedicle anchor 21; such that, when the handle 921 rotates, the driver head 923 will also drive the pedicle anchor 21 to rotate. The upper hanger 924 and the lower hanger 925 are both furnished on the long-rod portion 922. Wherein, the lower hanger 925 is furnished on the long-rod portion 922 at a position corresponding to the upper hanger 924 across the axis; in addition, the distance between the lower end of the upper hanger 924 and the driver head 923 is greater than the distance between the lower end of the lower hanger 925 and the driver head 923. In other words, the upper and lower hangers 924 and 925 are located on opposite sides of the long-rod portion 922 and present a "one higher" and "one lower" configuration. Which mean, the upper hanger 924 is located higher than the lower hanger 925. In addition, when the driver head 923 is coupled to the fitting structure 214 of the pedicle anchor 21, the position of the upper hanger 924 exactly corresponds to the position of the upper opening 2151 of the pedicle anchor 21, in the meantime, the position of the lower hanger 925 exactly corresponds to the position of the lower opening 2152 of the pedicle anchor 21. Therefore, when performing an operation, the surgeon only needs to observe the position or rotation angle of the upper and lower hangers 924 and 925, he/she will know the current position or rotation angle of the upper and lower openings 2151 and 2152 of the pedicle anchor 21 being driven by the screwdriver 92. Moreover, the upper hanger 924 and the lower hanger 925 each has an elongated sheet which is connected to the long-rod portion by several convex posts, and the upper and lower ends of the elongated sheet are slightly protruding from the convex post in the axial direction. Furthermore, the upper end of the elongated sheet is provided with a recess. The structural design of the upper and lower hangers allows the two ends of the suspension ligament 23 extending from the upper and lower openings of the oblique through hole of the pedicle anchor to be respectively wound and hung on the convex posts of the upper and lower hangers 924 and 925, and also allows the two ends of the suspension ligament 23 to be inserted in the recesses of the upper and lower hangers 924 and 925, so as to avoid the situation that the suspension ligament 23 is entangled by itself or entangled on the screwdriver 92 when the screwdriver 92 is operated to rotate the pedicle anchor 21.

Figure 15:
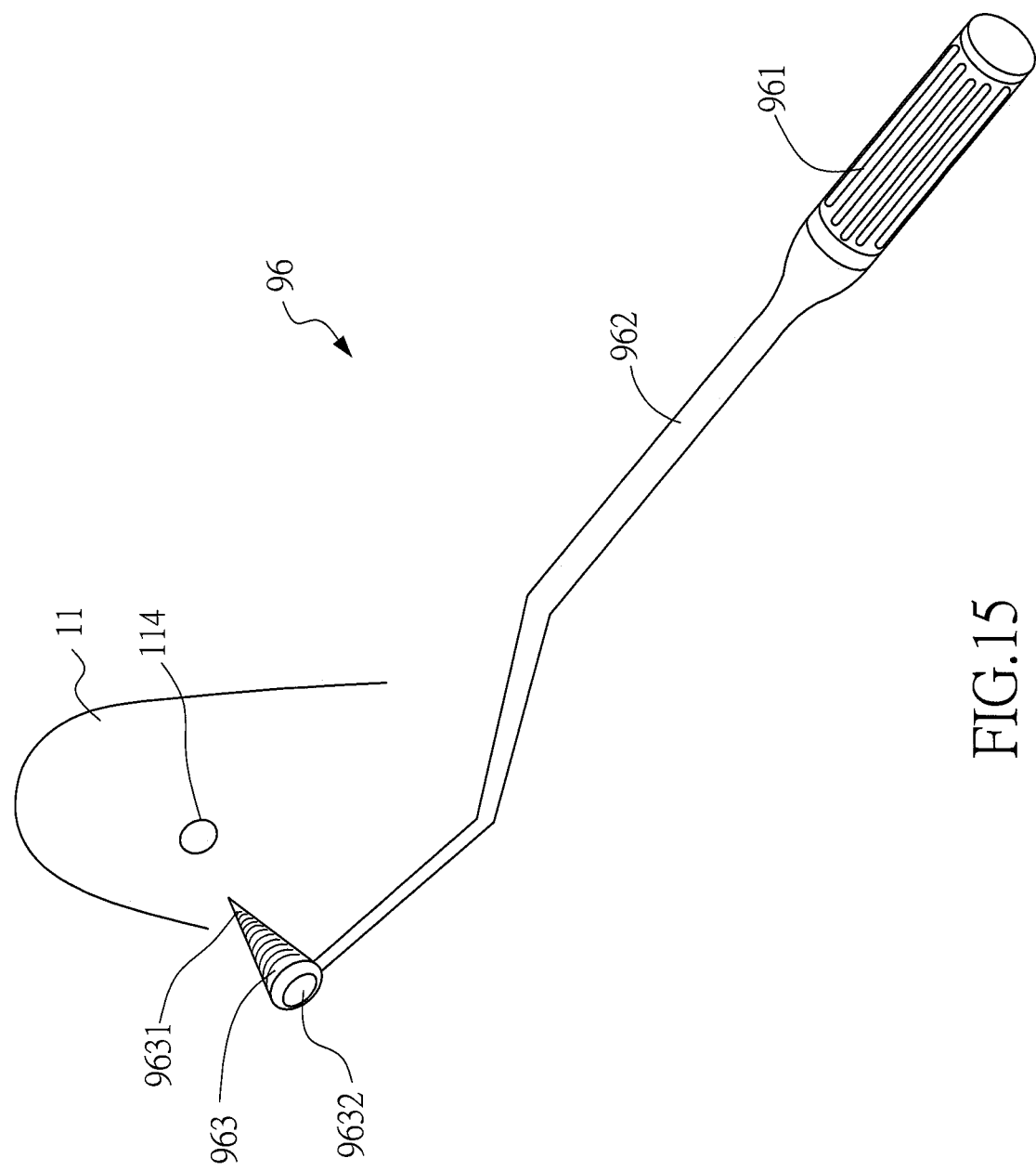
FIG. 15 is a schematic diagram of an embodiment of the hand-held file in the component set of the T-PAS system of the present invention.

Please refer to FIG. 15, which is a schematic diagram of an embodiment of the hand-held file in the component set of the T-PAS system of the present invention. In the present invention, a manual drill (i.e., Laminar Drill Guide) will be used to drill a tunnel on the lamina of the upper vertebral segment. Because the tunnel just drilled out often has sharp edges or cracks, it is easy to scratch the suspension ligament or break due to the tension of the suspension ligament. Therefore, the present invention discloses an innovative hand-held file 96 for smoothing the inner surface and the edge of the tunnel. The hand-held file 96 includes: a handle 961, a long-pole portion 962, and a conical file head 963. The long-pole portion 962 extends a predetermined length from one end of the handle 961 along an axis. The conical file head 963 is located at an end of the long-pole portion 962 away from the handle 961. The conical file head 963 is a cone-shaped structure and its protruding direction is approximately perpendicular to the axial direction. The surface of the conical file head 963 is a rough surface to provide the function of a file. The conical file head 963 has a sharp tip 9631 and a pressure end 9632. The size of the sharp tip 9631 is smaller than the diameter of the aperture of the tunnel. The pressure end 9632 is located at the tail end of the conical file head 963, which is the location where it connects with the long-pole portion 962. The pressure end 9632 is designed as a shallow concave on the surface of the tail end away from the sharp tip 9631. The shallow concave of the pressure end 9632 is convenient for the operator's finger (e.g., thumb) to press on the tail end surface of the pressure end 9632 to apply pressure to the conical file head 963; and then, the operator can simultaneously swing the handle 961 in order to drive the handle 961 to swing about the conical file head 963 as a pivot. So that, the rough surface of the conical file head 963 can rub the edge and inner surface of the tunnel, so as to achieve the effect of smoothing the inner surface and the edge of the tunnel.

Figure 16:
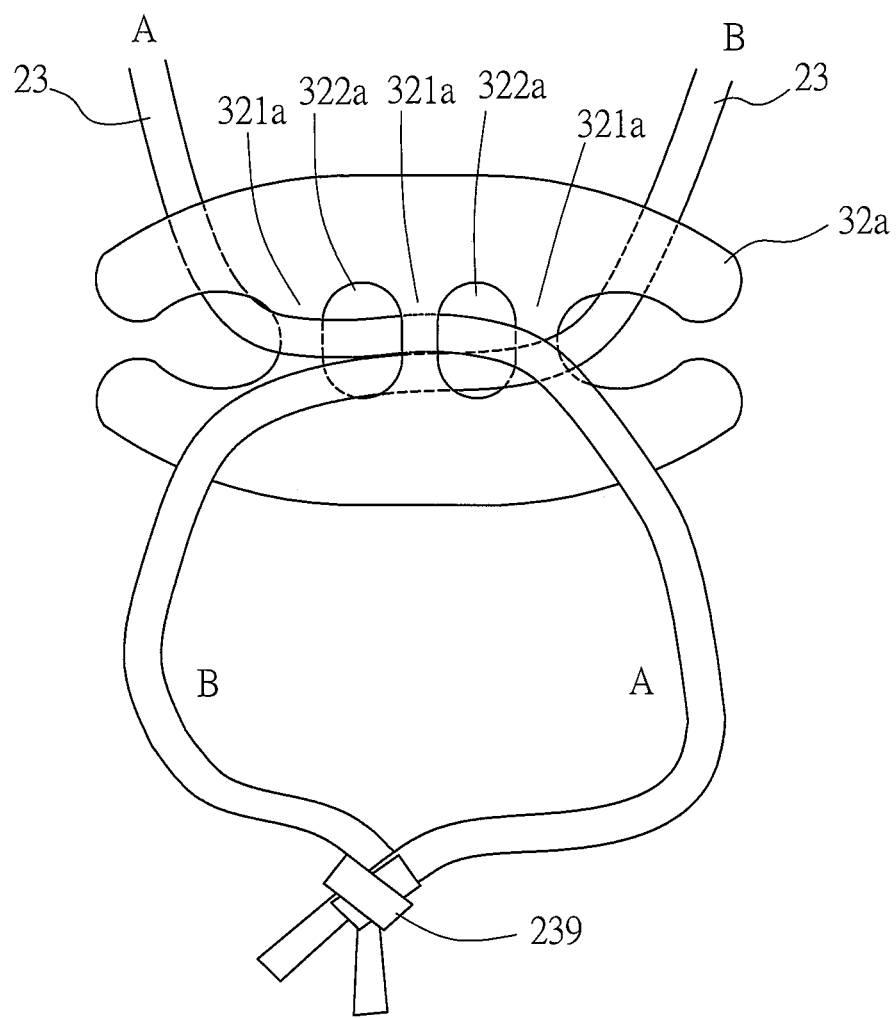
FIG. 16 is a schematic diagram showing an embodiment of a method to tie the suspension ligament on another kind of washer of the T-PAS system of the present invention.

Please refer to FIG. 16, which is a schematic diagram showing an embodiment of a method to tie the suspension ligament on another kind of washer of the T-PAS system of the present invention. The structure of the washer 32a shown in this embodiment is almost the same as the washer 32 shown in FIG. 10A and FIG. 10B, and the way to use is also similar. The only difference between these two washers is that, the washer 32a shown in FIG. 16 is provided with three bar portions 321a and two openings 322a formed between the three bar portions 321a. In this embodiment, the suspension ligament 23 first passes through the through hole of the pedicle screw (not shown in this figure) such that the pedicle screw is substantially hung on a middle portion of the suspension ligament 23. Then, the free ends of the two strips "A" and "B" of the suspension ligament 23 pass through the tunnel of the lamina (not shown in this figure). After that, the free ends of the two strips "A" and "B" of the suspension ligament 23 pass across the bar portions 321a and the two openings 322a from two sides of the washer 32a and then are tied up with at least 5 knots 239 to ensure the stability of connection between the suspension ligament 23 and the washer 32a.

While the present invention has been particularly shown and described with reference to a preferred embodiment, it will be understood by those skilled in the art that various changes in form and detail may be without departing from the spirit and scope of the present invention.

What is claimed is:

1. A translaminar pedicle anchor suspension system (T-PAS system) capable of being adapted to be installed in a spine having at least an upper vertebral segment and a lower vertebral segment; the T-PAS system comprising:

at least one pedicle anchor, capable of being adapted to be fixed to one of two pedicles of the lower vertebral segment; and at least one suspension ligament, one end of the suspension ligament being fixed to the pedicle anchor and thus adapted to be fixed to the pedicle of the lower vertebral segment, the other end of the suspension ligament being connected to a contralateral side-surface of a lamina of the upper vertebral segment by a connecting means; the suspension ligament configured to be tightened to a predetermined tension, such that the upper vertebral segment is able to be suspended by combination of the pedicle anchor and the suspension ligament from the lower vertebral segment below;

wherein each of the upper vertebral segment and the lower vertebral segment respectively includes: said lamina and two said pedicles respectively located on left and right sides of the lamina; the lamina of the upper vertebral segment is adapted to be provided with a tunnel penetrating left and right side-surfaces of the lamina;

wherein the T-PAS system further comprises at least one washer which is adapted to be located near the tunnel of the lamina of the upper vertebral segment; the washer has a length greater than the diameter of the tunnel to enable a predetermined tension to be applied to the suspension ligament and said other end of the suspension ligament is configured to be fixed at a location near the tunnel of the lamina of the upper vertebral segment;

wherein said connecting means is configured to pass said the other end of the suspension ligament through the tunnel of the lamina of the upper vertebral segment and connect to the washer;

wherein, the suspension ligament has two open ends and a middle section located between said two open ends; said middle section of the suspension ligament is configured to pass through the tunnel of the lamina of the upper vertebral segment to form a closed end at the middle section of the suspension ligament; the closed end of the suspension ligament is placed on a bar portion of the washer; wherein, when a pulling force is applied from the open ends of the suspension ligament, the washer is adapted to press against the side-surface near the tunnel of the lamina of the upper vertebral segment, such that the closed end of the suspension ligament is fixed to the side-surface of the lamina of the upper vertebral segment by means of the washer;

wherein, the pedicle anchor has an elongated columnar body extending along a central axis, an external thread arranged on an outer surface of the columnar body, a fitting structure arranged at a top end of the columnar body, and an oblique through hole penetrating through the columnar body; wherein, the oblique through hole passes through the central axis; an upper opening and a lower opening are formed at opposite ends of the through hole; a distance between the upper opening and the top end of the columnar body is smaller than another distance between the lower opening and the top end of the columnar body; the oblique through hole allows the suspension ligament to pass through, so that the pedicle anchor can be hung on the suspension ligament; the fitting structure can be connected with a screwdriver, such that, by operating the screwdriver, the pedicle anchor is driven to rotate about the central axis, and the pedicle anchor is adapted to be screwed and fixed to the pedicle.

2. The translaminar pedicle anchor suspension system of claim 1, wherein the at least one pedicle anchor comprises two pedicle anchors configured to be received in the left and right pedicles of the lower vertebral segment;

wherein the at least one washer comprises two washers adapted to be respectively located at left and right ends of the tunnel of the lamina of the upper vertebral segment;

wherein the at least one suspension ligament comprises first and second suspension ligaments; wherein one end of the first suspension ligament is fixed to the pedicle anchor configured to be located in the left pedicle, the other end of the first suspension ligament is adapted to be passed through the tunnel from the left side-surface to the right side-surface of the lamina of the upper vertebral segment and connected to the washer configured to be located at the right side-surface of the laminar; and wherein one end of the second suspension ligament is fixed to the pedicle anchor configured to be located in the right pedicle, the other end of the second suspension ligament is adapted to be passed through the tunnel from the right side-surface to the left side-surface of the lamina of the upper vertebral segment and connected to the washer configured to be located at the left side-surface of the laminar.

3. The translaminar pedicle anchor suspension system of claim 1, further comprising a sleeve capable of being adapted to be plugged in the tunnel; wherein, the suspension ligament is an artificial ligament; and wherein the pedicle anchor is a screw.

4. The translaminar pedicle anchor suspension system of claim 1, wherein, the external thread provided on the outer surface of the columnar body of the pedicle anchor includes a smaller-pitched threaded portion and a larger-pitched threaded portion; the smaller-pitched threaded portion is disposed closer to the top end of the columnar body; the larger-pitched threaded portion is disposed away from the top end of the columnar body; the upper opening and the lower opening are both located at the smaller-pitched threaded portion; a U-shaped rod-holding rack is provided at the top end of the columnar body of the pedicle anchor.

5. The translaminar pedicle anchor suspension system of claim 1, wherein:

the suspension ligament is configured to be folded into a double-line side-by-side structure and has said closed end at the folded middle section and said open ends away from the closed end;

the closed end of the folded suspension ligament is configured to pass through the upper opening of the oblique through hole and exit from the lower opening of the oblique through hole, such that the closed end of the folded suspension ligament is located out of the lower opening of the oblique through hole of the pedicle anchor; the open ends of the folded suspension ligament are located out of the upper opening of the oblique through hole of the pedicle anchor;

a lower part of the columnar body of the pedicle anchor is configured to be screwed into the pedicle of the lower vertebral segment in order to make the lower opening of the pedicle anchor close to but still exposed on the outer surface of the pedicle of the lower vertebral segment; wherein, the suspension ligament is applied with a relatively small first tension by gently applying a slight pulling force from the open ends of the suspension ligament;

when the pedicle anchor is adapted to be gradually screwed into the pedicle of the lower vertebral segment, the lower opening of the pedicle anchor is configured to be embedded in the pedicle of the lower vertebral segment, such that the suspension ligament is configured to wind around the outer surface of the pedicle anchor and thus adapted to be clamped between the outer surface of the pedicle anchor and the inside of the pedicle of the lower vertebral segment; therefore, the suspension ligament is further pulled by a larger force in order to tighten up the suspension ligament to reach and maintain a relatively larger second tension; the second tension is much greater than the first tension and is the predetermined tension when the T-PAS system is completely installed.

6. The translaminar pedicle anchor suspension system of claim 1, wherein:

the suspension ligament is configured to have one of its open ends to pass through the lower opening of the oblique through hole and exit from the upper opening of the oblique through hole, such that the two open ends of the suspension ligament are respectively exposed out of the lower opening and the upper opening: wherein, the middle section and the closed end of the suspension ligament are both located at a portion of the suspension ligament exposed out of the upper opening of the oblique through hole of the pedicle anchor;

a lower part of the columnar body of the pedicle anchor is configured to be screwed into the pedicle of the lower vertebral segment, such that the lower opening together with a part of the suspension ligament extended out from the lower opening are configured to be screwed into and clamped between the outer surface of the pedicle anchor and the pedicle of the lower vertebral segment; the open end of the suspension ligament exposed out of the upper opening of the oblique through hole of the pedicle passes through said part of the suspension ligament from below at a location near the upper opening; wherein, the suspension ligament is applied with a relatively small first tension by gently applying a slight pulling force from the open end of the suspension ligament exposed out of the upper opening;

when the pedicle anchor is adapted to be gradually screwed into the pedicle of the lower vertebral segment, the upper opening of the pedicle anchor is configured to be embedded in the pedicle of the lower vertebral segment, such that the part of the suspension ligament is configured to wind around the outer surface of the pedicle anchor and thus adapted to be clamped between the outer surface of the pedicle anchor and the inside of the pedicle of the lower vertebral segment; therefore, the suspension ligament is further pulled by a larger force in order to tighten up the suspension ligament to reach and maintain a relatively larger second tension; the second tension is much greater than the first tension and is the predetermined tension when the T-PAS system is completely installed.

7. A pedicle anchor for use in a translaminar pedicle anchor suspension system; said pedicle anchor being capable of being adapted to be fixed to a pedicle of a vertebra; said pedicle anchor comprising:

an elongated columnar body extending along a central axis;

an external thread arranged on an outer surface of the columnar body;

a fitting structure arranged at a top end of the columnar body; and a through hole penetrating through the columnar body; wherein, the through hole is not parallel to the central axis; the through hole passes through the central axis; the through hole allows a suspension ligament to pass through, so that the pedicle anchor can be hung on the suspension ligament; the fitting structure can be connected with a screwdriver, such that, by operating the screwdriver, the pedicle anchor can be driven to rotate about the central axis, and the pedicle anchor together with the suspension ligament are adapted to be screwed and fixed to the pedicle;

wherein, the through hole is an oblique through hole; an upper opening and a lower opening are formed at opposite ends of the through hole; a distance between the upper opening and the top end of the columnar body is smaller than another distance between the lower opening and the top end of the columnar body; the external thread provided on the outer surface of the columnar body of the pedicle anchor includes a smaller-pitched threaded portion and a lamer-pitched threaded portion; the smaller-pitched threaded portion is disposed closer to the top end of the columnar body; the larger-pitched threaded portion is disposed away from the top end of the columnar body; the upper opening and the lower opening are both located at the smaller-pitched threaded portion.

8. The pedicle anchor of claim 7, wherein:

the suspension ligament has two open ends and a middle section; the suspension ligament is configured to be folded into a double-line side-by-side structure and has a closed end at the folded middle section;

the closed end of the folded suspension ligament is configured to pass through the upper opening of the oblique through hole and exit from the lower opening of the oblique through hole, such that the closed end of the folded suspension ligament is located out of the lower opening of the oblique through hole of the pedicle anchor; the open ends of the folded suspension ligament are located out of the upper opening of the oblique through hole of the pedicle anchor;

a lower part of the columnar body of the pedicle anchor is configured to be screwed into the pedicle of the lower vertebral segment in order to make the lower opening of the pedicle anchor close to but still exposed on the outer surface of the pedicle of the lower vertebral segment; wherein, the suspension ligament is applied with a relatively small first tension by gently applying a slight pulling force from the open ends of the suspension ligament;

when the pedicle anchor is adapted to be gradually screwed into the pedicle of the lower vertebral segment, the lower opening of the pedicle anchor is configured to be embedded in the pedicle of the lower vertebral segment, such that the suspension ligament is configured to wind around the outer surface of the smaller-pitched thread portion of the pedicle anchor and thus adapted to be clamped between the outer surface of the pedicle anchor and the inside of the pedicle of the lower vertebral segment; therefore, the suspension ligament is further pulled by a larger force in order to tighten up the suspension ligament to reach and maintain a relatively larger second tension; the second tension is much greater than the first tension.

9. The pedicle anchor of claim 7, wherein:

the suspension ligament has two open ends and a middle section; said suspension ligament is configured to have one of its open ends to pass through the lower opening of the oblique through hole and exit from the upper opening of the oblique through hole, such that the two open ends of the suspension ligament are respectively exposed out of the lower opening and the upper opening; wherein, the middle section and a closed end of the suspension ligament are both located at a portion of the suspension ligament exposed out of the upper opening of the oblique through hole of the pedicle anchor;

a lower part of the columnar body of the pedicle anchor is configured to be screwed into the pedicle of the lower vertebral segment, such that the lower opening together with a part of the suspension ligament extended out from the lower opening are configured to be screwed into and clamped between the outer surface of the pedicle anchor and the pedicle of the lower vertebral segment; the open end of the suspension ligament exposed out of the upper opening of the oblique through hole of the pedicle passes through said part of the suspension ligament from below at a location near the upper opening; wherein, the suspension ligament is applied with a relatively small first tension by gently applying a slight pulling force from the open end of the suspension ligament exposed out of the upper opening;

when the pedicle anchor is adapted to be gradually screwed into the pedicle of the lower vertebral segment, the upper opening of the pedicle anchor is configured to be embedded in the pedicle of the lower vertebral segment, such that the part of the suspension ligament is configured to wind around the outer surface of the pedicle anchor and thus adapted to be clamped between the outer surface of the pedicle anchor and the inside of the pedicle of the lower vertebral segment; therefore, the suspension ligament is further pulled by a larger force in order to tighten up the suspension ligament to reach and maintain a relatively larger second tension; the second tension is much greater than the first tension.

10. A component set for use in a translaminar pedicle anchor suspension system (T-PAS system) capable of being adapted to be installed on a spine having at least an upper vertebral segment and a lower vertebral segment; said component set comprising:

at least one pedicle anchor, capable of being adapted to be fixed to one of two pedicles of the lower vertebral segment;

at least one washer, capable of being adapted to be located on a lamina of the upper vertebral segment;

at least one suspension ligament, for connecting the pedicle anchor and the washer, the suspension ligament being adapted to be fixed to both the pedicle of the lower vertebral segment and the lamina of the upper vertebral segment by means of the pedicle anchor and the washer; in addition, the suspension ligament is pre-assembled on the pedicle anchor; and a screwdriver, capable of being connected to the pedicle anchor, such that the pedicle anchor is adapted to be screwed into the pedicle of the lower vertebral segment by operating the screwdriver;

wherein said pedicle anchor comprises:

an elongated columnar body extending along a central axis;

an external thread arranged on an outer surface of the columnar body;

a fitting structure arranged at a top end of the columnar body; and an oblique through hole penetrating through the columnar body;

wherein, the oblique through hole passes through the central axis; an upper opening and a lower opening are formed at opposite ends of the oblique through hole; a distance between the upper opening and the top end of the columnar body is smaller than another distance between the lower opening and the top end of the columnar body; the oblique through hole allows the suspension ligament to pass through, so that the pedicle anchor can be hung on the suspension ligament; the fitting structure can be connected with the screwdriver, such that, by operating the screwdriver, the pedicle anchor can be driven to rotate about the central axis, and the pedicle anchor together with the suspension ligament are adapted to be screwed and fixed to the pedicle.

11. The component set of claim 10, wherein, the external thread provided on the outer surface of the columnar body of the pedicle anchor includes a smaller-pitched threaded portion and a larger-pitched threaded portion; the smaller-pitched threaded portion is disposed closer to the top end of the columnar body; the larger-pitched threaded portion is disposed away from the top end of the columnar body; the upper opening and the lower opening are both located at the smaller-pitched threaded portion; a U-shaped rod-holding rack is provided at the top end of the columnar body of the pedicle anchor.

12. The component set of claim 10, wherein, the lamina of the upper vertebral segment is adapted to be provided with a tunnel penetrating left and right side-surfaces of the lamina; the suspension ligament is an artificial ligament; the suspension ligament has two open ends and a middle section located between said two open ends; said middle section of the suspension ligament is configured to pass through the tunnel of the lamina of the upper vertebral segment to form a closed end at the middle section of the suspension ligament; the closed end of the suspension ligament is placed on a bar portion of the washer; wherein, when a pulling force is applied from the open ends of the suspension ligament, the washer is adapted to press against the side-surface near the tunnel of the lamina of the upper vertebral segment, such that the closed end of the suspension ligament is fixed to the side-surface of the lamina of the upper vertebral segment by means of the washer.

13. The component set of claim 12, wherein:

the suspension ligament is configured to be folded into a double-line side-by-side structure and has said closed end at the folded middle section and said open ends away from the closed end;

the closed end of the folded suspension ligament is configured to pass through the upper opening of the oblique through hole and exit from the lower opening of the oblique through hole, such that the closed end of the folded suspension ligament is located out of the lower opening of the oblique through hole of the pedicle anchor; the open ends of the folded suspension ligament are located out of the upper opening of the oblique through hole of the pedicle anchor.

14. The component set of claim 12, wherein, the suspension ligament is configured to have one of its open ends to pass through the lower opening of the oblique through hole and exit from the upper opening of the oblique through hole, such that the two open ends of the suspension ligament are respectively exposed out of the lower opening and the upper opening; wherein, the middle section and the closed end of the suspension ligament are both located at a portion of the suspension ligament exposed out of the upper opening of the oblique through hole of the pedicle anchor.

15. The component set of claim 10, wherein the screwdriver includes:

a handle;

a long-rod portion, extending a predetermined length from one end of the handle along an axis;

a driver head, located at an end of the long-rod portion away from the handle; the driver head can be connected with the fitting structure of the pedicle anchor, such that, when the handle rotates, the driver head will also drive the pedicle anchor to rotate;

an upper hanger, furnished on the long-rod portion; and a lower hanger, furnished on the long-rod portion; wherein, the lower hanger is furnished on the long-rod portion at a position corresponding to the upper hanger across the axis; in addition, the distance between the upper hanger and the driver head is greater than the distance between the lower hanger and the driver head;

wherein, when the driver head is coupled to the fitting structure of the pedicle anchor, the position of the upper hanger exactly corresponds to the position of the upper opening of the pedicle anchor, in the meantime, the position of the lower hanger exactly corresponds to the position of the lower opening of the pedicle anchor; the upper and lower hangers allows the two ends of the suspension ligament extending from the upper and lower openings of the oblique through hole of the pedicle anchor to be respectively wound and hung on the upper and lower hangers.

* * * * *